US005637106A

United States Patent [19]
Mitchell et al.

[11] Patent Number: 5,637,106
[45] Date of Patent: Jun. 10, 1997

[54] ABSORBENT PRODUCT FOR PERSONAL USE

[75] Inventors: Winalee G. Mitchell, deceased, late of Phoenix, Ariz., by James G. Mitchell, legal representative; Paul S. Rankin, Bowling Green; Andrew J. Szypka, Curtice, both of Ohio

[73] Assignee: Carol M. Stocking, Perrysburg, Ohio

[21] Appl. No.: 342,266

[22] Filed: Nov. 17, 1994

Related U.S. Application Data

[63] Continuation-in-part of Ser. No. 902,510, Jun. 23, 1992, abandoned, which is a continuation of Ser. No. 794,793, Nov. 19, 1991, abandoned, which is a continuation of Ser. No. 698,247, May 6, 1991, abandoned, which is a continuation of Ser. No. 372,030, Jun. 27, 1989, abandoned, which is a continuation-in-part of Ser. No. 352,491, May 16, 1989, abandoned, which is a continuation-in-part of Ser. No. 272,160, Nov. 16, 1988, abandoned.

[51] Int. Cl.$^6$ ..................................... A61F 13/15
[52] U.S. Cl. ..................... 604/368; 604/369; 604/379
[58] Field of Search ........................... 604/366, 364, 604/370, 385.1, 368, 369

[56] References Cited

U.S. PATENT DOCUMENTS 5,072,687  12/1991  Mitchell et al. ..................... 118/37

Primary Examiner—John G. Weiss
Assistant Examiner—David J. Cho
Attorney, Agent, or Firm—David C. Purdue; John C. Purdue

[57] ABSTRACT

Several embodiments of an improved absorbent insert or core are disclosed. According to one embodiment, the insert comprises a fluff layer physically integrated to at least one layer of laminate consisting of at least one tissue layer and polymer powder secured to it and supported on it. The fluff layer and the laminate are embossed between rollers that physically integrate the two layers and produce transfer sites through which liquid is rapidly transferred into the fluff layer, away from a wearer. In another embodiment, an absorbent insert is produced by embossing a laminate between a smooth roller and a patterned roller and trimming and folding the embossed laminate to produce an insert with a central region with an exposed pattern of embossed depressions and, on each side of the central region, lateral regions with an exposed, smooth surface. According to another embodiment, an absorbent insert is produced by depositing super absorbent polymer powder on a portion of a layer of fluff, covering the powder with at least one tissue layer, and embossing the assembly to produce an integrated absorbent insert. According to another embodiment, an absorbent insert is produced by depositing super absorbent polymer powder on a portion of a layer of fluff, covering at least a portion of the fluff with polymer deposited thereon with at least one laminate layer, and embossing the assembly to produce an integrated absorbent insert.

20 Claims, 11 Drawing Sheets

ABSORBENT PRODUCT FOR PERSONAL USE

REFERENCE TO RELATED APPLICATIONS

This is a continuation in part of, and was copending with, application Ser. No. 07/902,510, filed Jun. 23, 1992, as a continuation of application Ser. No. 07/794,793, filed Nov. 19, 1991, as a continuation of application Ser. No. 07/698,247, filed May 6, 1991, itself a continuation of application Ser. No. 07/372,030, filed Jun. 27, 1989 as a continuation in part of application Ser. No. 07/352,491, filed May 16, 1989, itself a continuation in part of application Ser. No. 07/272,160, filed Nov. 16, 1988. All of the foregoing applications are now abandoned.

BACKGROUND OF THE INVENTION

1. Field of the Invention

This invention relates to the field of absorbent products, especially for use by persons with incontinence. Specifically, the invention is concerned with diapers or underpants type products, as well as absorbent pads and the like, which are highly absorptive due to the inclusion of a super absorbent polymer in an embossed target area.

2. Description of the Prior Art

There has been a great deal of recent development in the field of personal absorbent products ranging from diapers for infants to adult briefs for people with urinary incontinence. One major area of development has been broadly in the field of super absorbent polymers, such as starches, acrylics modified cellulose, gums and the like. In some respects, the super absorbent polymers are far superior to cellulose fluff and other conventional absorbent media used in personal absorbent products. For example, the polymers, on a weight basis, have an absorption capacity which is far greater than fluff. In addition, super absorbent polymers retain absorbed liquid, even under pressure, far better than fluff which is subject to "squeeze-out" where absorbed liquid is released from fluff when it is subjected to pressure.

There are some drawbacks, however, to super absorbent polymers as components of personal absorbent products. Generally, super absorbent polymers are inferior to fluff in terms of rate of absorption of liquid. Another drawback of super absorbent polymers is their susceptibility to what is referred to as "gel-blocking" where a layer containing super absorbent polymer is wetted, the polymer absorbs the liquid and the gelled polymer, which has expanded to many times its dry size, blocks additional liquid from entering the layer.

Super absorbent polymers, because they are finely powdered, present manufacturing difficulties in terms of satisfactorily incorporating into absorbent products.

Super absorbent polymers have been incorporated into absorbent products in a variety of ways. In some cases, super absorbent polymer is sprinkled into a fluff layer or deposited between two fluff layers, as disclosed in U.S. Pat. No. 4,381,782, but these approaches are plagued by problems arising from the migration of the powder from the place it is deposited. Another approach entails the use of tissue with super absorbent polymer powder fixed to it. Such tissue, also known as laminate, has been used in absorbent products alone and in combination with conventional fluff.

Examples of the use of laminate alone are shown in U.S. Pat. No. 4,568,341. This patent discloses a special laminate structure including undulations and small hinge and flap members formed in the laminate. This laminate structure compensates for the relatively slow absorbency rate of the super absorbent polymer in the laminate.

Composite absorbent products including one or more layers of laminate and one or more layers of fluff are disclosed in U.S. Pat. Nos. 3,888,256, 4,333,465, 4,411,660, 4,592,751, 4,622,036, 4,643,726 and 4,699,619.

U.S. Pat. No. 4,055,180 discloses an absorbent article including super absorbent polymer powder disposed in pockets formed in an absorbent pad.

A product distributed under the trademark Slimline comprises a backing sheet, a facing sheet, a layer of laminate adjacent to the facing sheet and a layer of fluff between the laminate and the backing sheet.

SUMMARY OF THE INVENTION

The instant invention is based upon the discovery of an improved absorbent article incorporating an improved absorbent insert or core. According to one embodiment of the invention, the insert comprises a fluff layer physically integrated to at least one layer of laminate. The insert is positioned in the absorbent article so that the laminate will be adjacent to a wearer. In a preferred embodiment, the fluff layer and the laminate are embossed between rollers that physically integrate the two layers and produce transfer sites through which liquid is rapidly transferred into the fluff layer, away from a wearer.

In another embodiment, an absorbent insert is produced by embossing a laminate between a smooth roller and a patterned roller and trimming and folding the embossed laminate. The insert is folded to produce an insert with a central region with an exposed pattern of embossed depressions and, on each side of the central region, lateral regions with an exposed, smooth surface.

In yet another embodiment, an absorbent insert is produced by depositing super absorbent polymer powder on a portion of a layer of fluff, covering the powder with at least one tissue layer, and embossing the assembly to produce an integrated absorbent insert with transfer sites through which liquid is rapidly transferred into the fluff layer, away from a wearer.

According to another embodiment, an absorbent insert is produced by depositing super absorbent polymer powder on a portion of a layer of fluff, covering at least a portion of the fluff with polymer deposited thereon with at least one laminate layer, and embossing the assembly to produce an integrated absorbent insert with transfer sites through which liquid is rapidly transferred into the fluff layer for absorption by the polymer powder dispersed in the fluff.

DETAILED DESCRIPTION OF THE INVENTION

Figure 1:
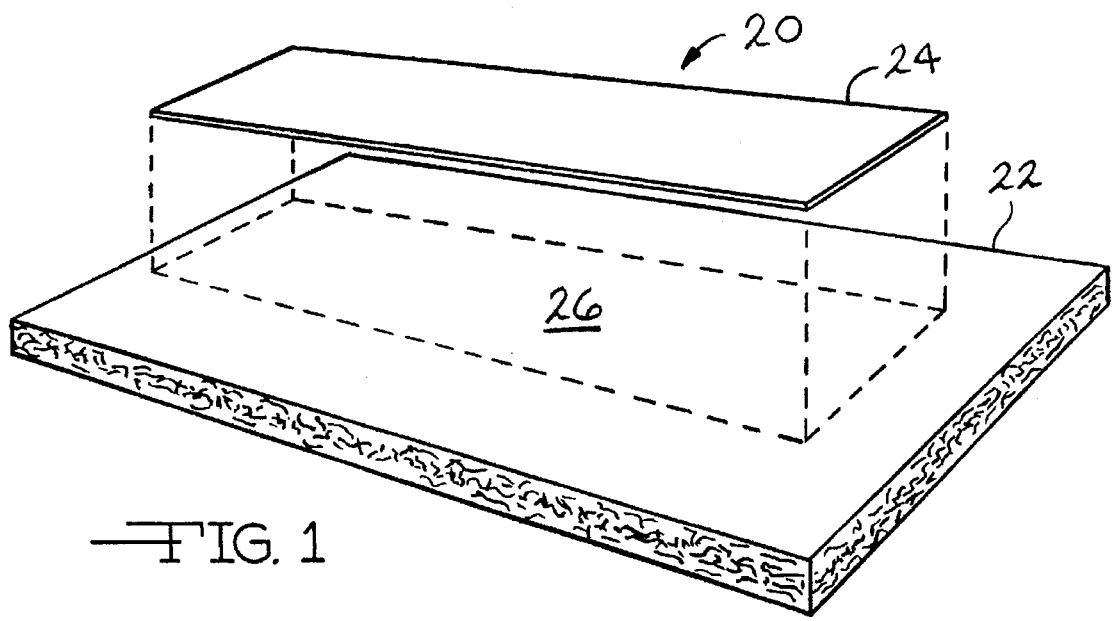
FIG. 1 is an exploded, perspective view of the absorptive components of one embodiment of an absorbent product according to the present invention.

Referring now to FIG. 1, absorptive components of one embodiment of an absorptive product are indicated generally at 20. One of the absorptive components 20 is a relatively thick, fluff layer of moisture absorbing material 22, such as cellulose fluff, fluffed wood pulp, batting or the like. The other one of the absorptive components 20 is a layer of laminate 24 comprising tissue with particles of a super absorbent polymer deposited thereon and secured thereto. A preferred material for the laminate layer 24 is a laminate containing a super absorbent polymer of the modified acrylic type. Such a laminate is available from Gelok International under the trademark "GELOK 6000 DOUBLE PLY/ DOUBLE PLY (1080)".

The laminate layer 24 is superposed on a central target area 26 of the fluff layer 22, as indicated by dotted lines in FIG. 1. The laminate layer 24 does not extend the full length or width of the fluff layer 22, although a larger laminate layer may be used. The laminate layer 24 has an extremely high absorption capacity but the laminate itself is relatively expensive. Accordingly, the laminate layer is advantageously restricted to the target area 26 which coincides with the area where urine voided by a wearer will first contact the absorptive product. In the target area 26, the need for absorptive capacity is the greatest and the laminate layer 24 meets this need.

Before the laminate layer 24 is deposited on the fluff layer 22, water is sprayed on the central region 26 of the fluff layer 22. The moisture serves to adhere the laminate layer 24 to the fluff layer 22 during subsequent assembly operations. The precise amount of water to be sprayed is not critical, but there should be enough water to provide some adhesion between the layers 22 and 24. On the other hand, the amount of water should be only enough to moisten the upper surface of the fluff layer 22; this amount of water, as is subsequently explained in more detail, significantly improves the properties of the final product.

Figure 2:
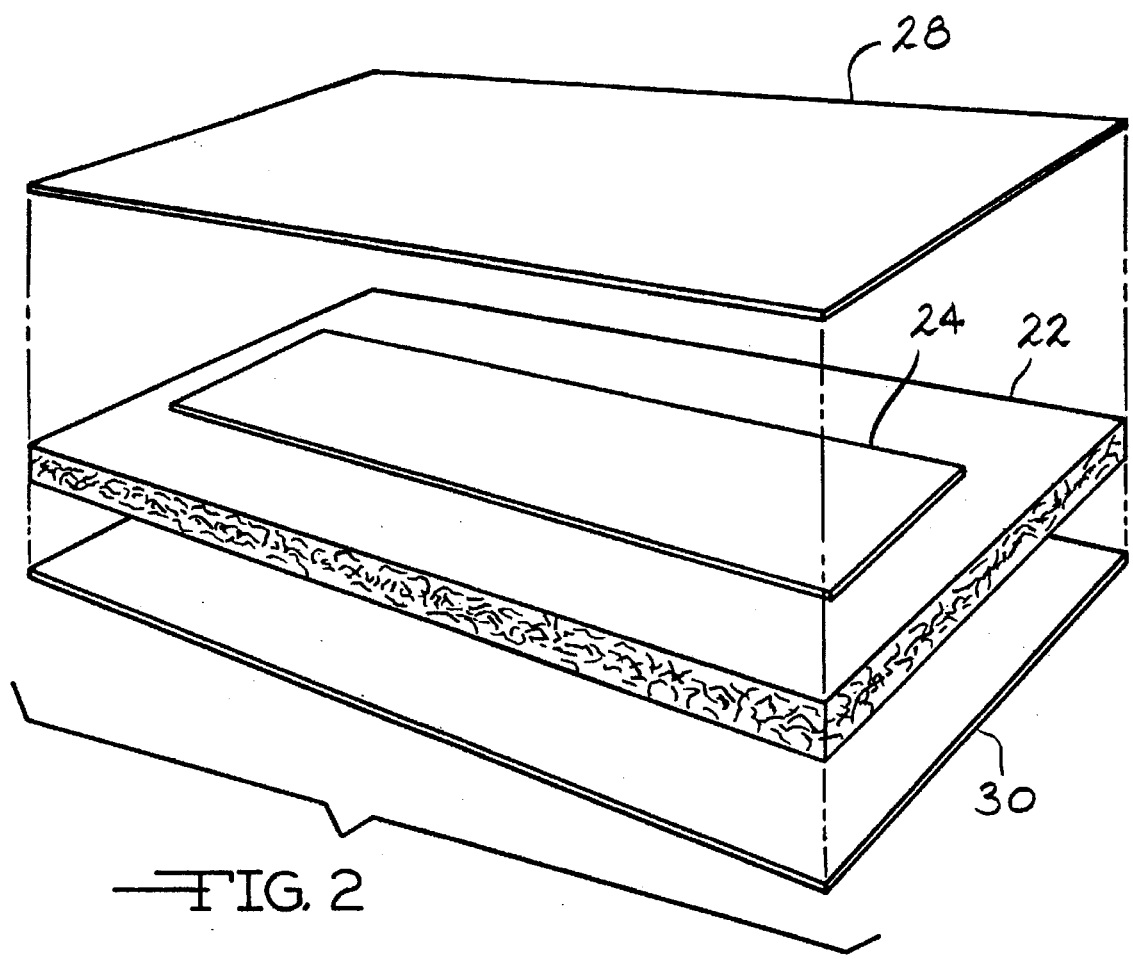
FIG. 2 is an exploded, perspective view of the absorptive components illustrated in FIG. 1, and upper and lower tissue layers.
Figure 3:
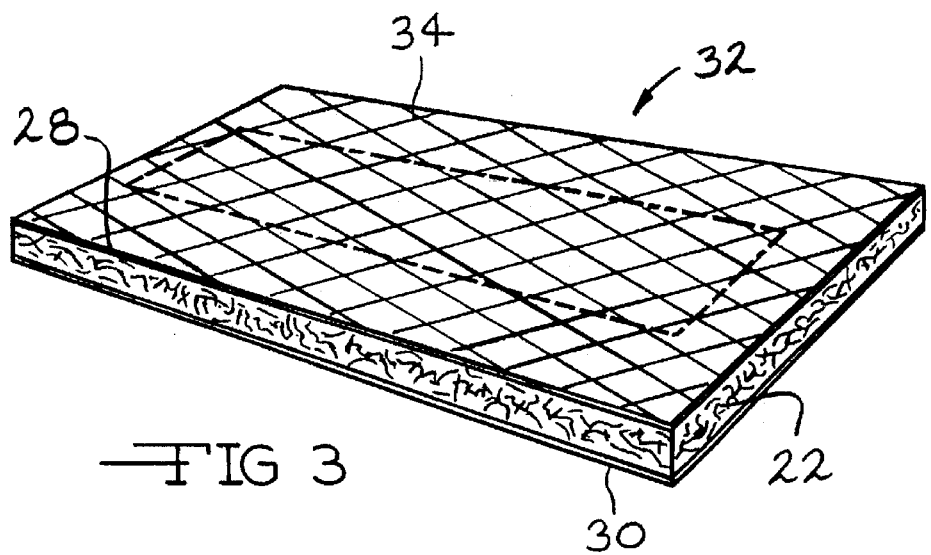
FIG. 3 is a perspective view of an absorbent core comprising the components illustrated in FIG. 2, after they have been integrated by an embossing operation.

After water has been sprayed on the fluff layer 22, the laminate layer 24 is deposited on the fluff layer 22 in the target area 26, as shown in FIG. 2. An upper layer of tissue 28 is positioned on top of the layers 22 and 24 while a lower layer of tissue 30 is positioned below the layer 22. After the tissue layers 28 and 30 are brought into contact with the absorbent core 20, the components are subjected to an embossing step. A smooth roller (not shown) is applied to the lower tissue layer 30 and a patterned roller (not shown) is applied to the opposed, upper tissue layer 28 to produce an embossed absorbent core 32. A suitable diamond embossing pattern is shown in FIG. 3, reflected in the pattern shown on the surface of the tissue layer 30. The embossing pattern on the embossing die (not shown) applied to the upper tissue layer 28 produces a pattern of channels 34 in the surface of the tissue layer 28, in the laminate layer 24, and in the fluff layer 22. As is explained below, these channels 34 constitute transfer sites through which liquid is absorbed quickly from above the upper tissue layer 28, through the laminate layer 24, to the fluff layer where it will be absorbed. The channels 34 are interconnected in a continuous network which promotes excellent wicking characteristics.

In the channels 34, there is a high density interface between the tissue layer 28, the laminate layer 24 and the fluff layer 22. In this interface, there is a physical bond between the layers 28, 24 and 22 which gives the absorbent core 32 physical integrity. In the areas between the channels 34, the layers 28, 24 and 22 have a lower density than these layers have in the channels 34.

The embossing step can be carried out advantageously with approximately 50 to 175 lbs of pressure per lineal inch of the embossing rollers. A variety of patterns would be suitable for the patterned embossing roller, beside the one reflected in the upper tissue layer 28 shown in FIG. 3. Particulars about the embossing pattern are discussed below in connection with some examples of the invention.

The embossing operation was carried out with and without the step of spraying water on the fluff layer. In the cases where no water was sprayed, the embossing step did not result in a physical bond between the fluff layer and the laminate layer. Rather, the laminate layer and the fluff layer remained discreet layers, like the layers in the prior art SLIMLINE product. However, when the embossing operation was carried out after water had been sprayed on the fluff layer, a physical bond was produced between the fluff layer and the laminate layer.

It will be appreciated that the manufacturing steps described above with reference to FIGS. 1–3 can be applied to bulk materials supplied, for example, from rolls. Specifically, the fluff layer 22, the laminate layer 24 and the tissue layers 28 and 30 can be manufactured into an embossed, absorbent core 32 of infinite length which can later be cut to appropriate length and incorporated into an absorbent product according to the instant invention. After the absorbent core 32 has been embossed, it is preferably subjected to a de-bulking operation in which it is passed between two compression rollers (not shown). This step adds further integrity to the embossed absorbent core 32 and promotes more economical packaging by producing thinner absorbent products.

Figure 4:
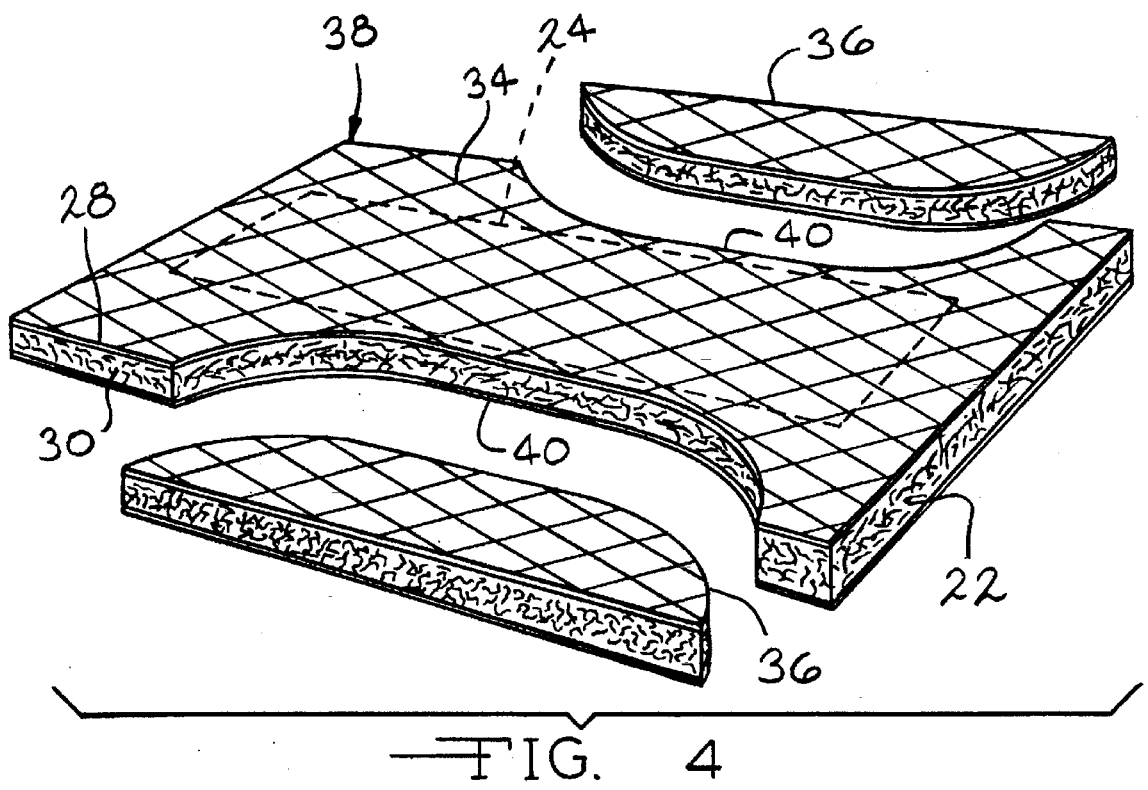
FIG. 4 is a perspective view of the absorbent core during a trimming operation.

Referring now to FIG. 4, the embossed absorbent core 32 is illustrated after ears 36 have been trimmed therefrom to produce an absorbent insert 38, with leg cut outs 40, for incorporation in an absorbent product. The cut outs 40 extend inwardly toward, but terminate just short of, the laminate layer 24. The ears 36 can be recycled, if desired, to yield material suitable for producing additional fluff layers 22. The trimming can be carried out with a die-cutter which may include a cutter for cutting the embossed absorbent core 32 to produce an absorbent insert 38 of a given length. Alternatively, a separate cutter may be used to cut absorbent core material to an appropriate length.

Figure 5:
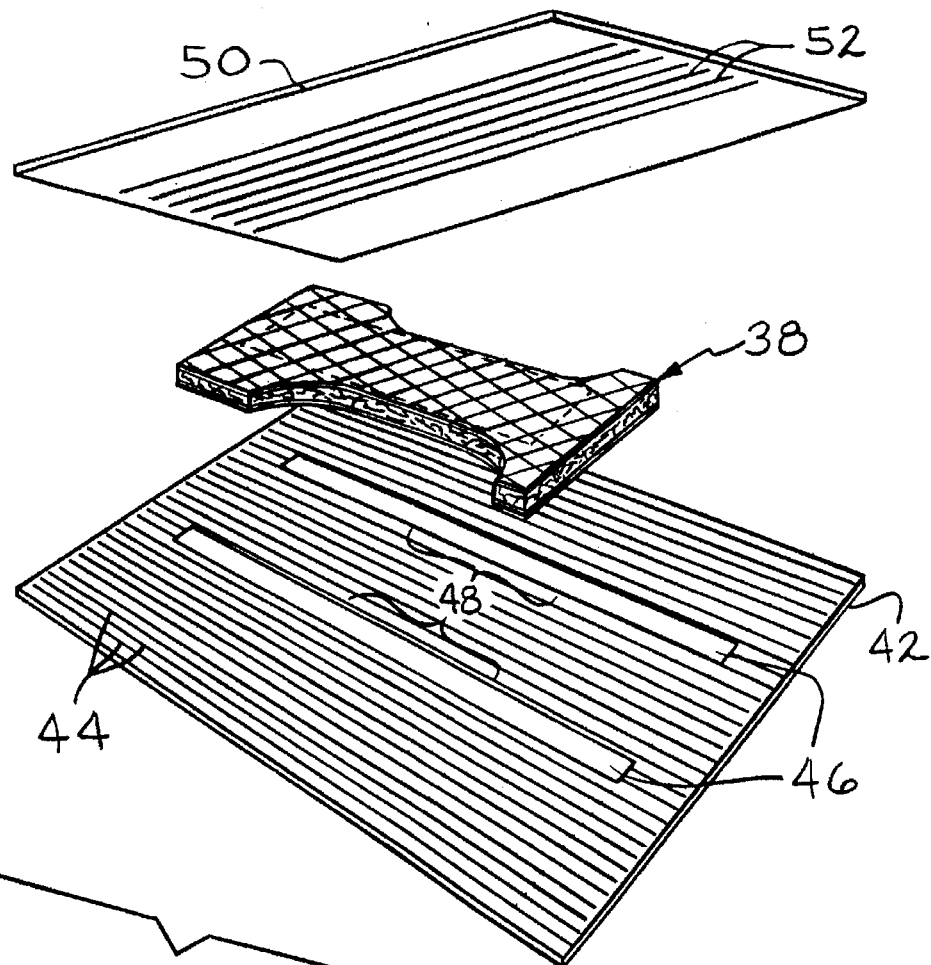
FIG. 5 is an exploded, perspective view of the components of one embodiment of an absorbent product incorporating the absorbent core illustrated in FIG. 4.

With reference to FIG. 5, a water impervious backing sheet 42 is illustrated below the absorbent insert 38. A plurality of lines 44 of a hot melt type adhesive are applied longitudinally to the backing sheet 42, across the entire width thereof. In the illustrated embodiment, elastic means 46 are secured to the backing sheet 42 in spaced, parallel relationship to one another. Preferably, the elastic means 46 comprise a plurality of individual elastic threads secured to the backing sheet 42 by an adhesive which is applied thereto and to the backing sheet 42. Then, a center portion 48 of the elastic means 46 is stretched, and the stretched elastic means 46 are applied to the adhesive on the backing sheet 42. When the adhesive sets and the stretching is relaxed, gathers 58 (FIG. 6) are formed by the center portion 48 of the elastic means 46.

Also shown in FIG. 5 is a facing sheet 50 which has the same length and width as the backing sheet. The facing sheet 50 is composed of a non-woven material through which liquid will readily pass for absorption in the absorbent insert 38. Several sprays 52 of hot melt adhesive are applied longitudinally to the facing sheet 50, over a central portion having a width corresponding generally with the width of the absorbent insert 38. With the lines 44 and sprays 52 of hot melt in place, the components shown in FIG. 5 are assembled by positioning the absorbent insert 38 centrally on the backing sheet 42 and positioning the facing sheet 50 thereon. After assembly, these components are passed between compression rollers (not shown) to promote good bonding therebetween.

Figure 6:
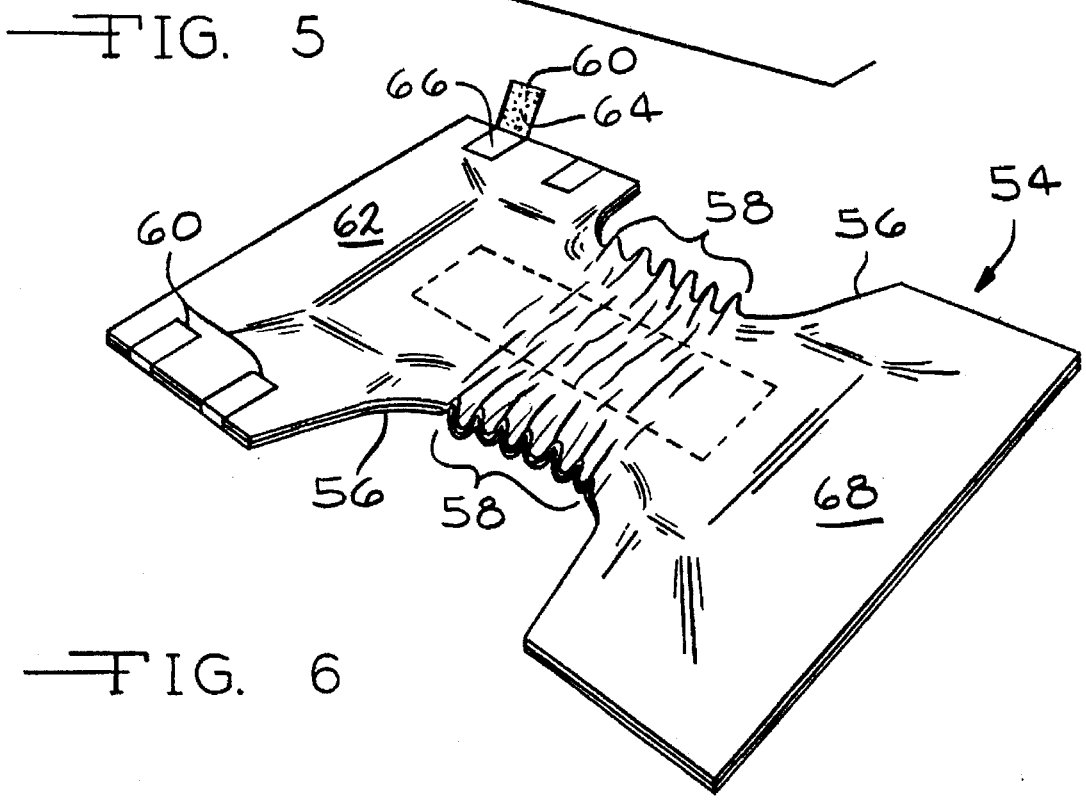
FIG. 6 is a perspective view of a completed absorbent product according to one embodiment of the present invention.

With reference to FIG. 6, an absorbent product 54 is illustrated after leg cut outs 56 have been trimmed therefrom. Gathers 58 are formed, adjacent to a central portion of the leg cut outs 56, by the central portion 48 (FIG. 5) of the elastic means 46. The gathers 58 serve to prevent leakage by promoting a snug fit of the absorbent product 54 around the legs of a wearer. Adhesive tab fasteners 60 are secured to a rear panel 62 of the absorbent product 54 in a known fashion. The tab fasteners 60 include an adhesive side 64 which remains secured to a release paper 66, until the absorbent product 54 is to be worn. With the absorbent product 54 positioned on a wearer, the tab fasteners 60 are lifted from the release paper 66 and the adhesive side 64 is applied to the outside of the backing sheet 42 on a front panel 68 of the absorbent product 54, thereby securing the absorbent product 54 to the wearer. Preferably, the adhesive on the side 64 of the tab fasteners is one which can be released from and refastened to the backing sheet 42, so that the tab fasteners 60 are refastenable.

EXAMPLE 1

An absorbent core corresponding with the core 32 was produced from cellulose fluff and GELOK 6000 DOUBLE PLY/DOUBLE PLY (1080) laminate. The super absorbent polymer in the laminate was a polyacrylate product which is distributed by Chemdal under the trade name ARIDALL 1080. The core was embossed with a 1 inch by 1 inch diamond pattern on an upper surface thereof. The channels had a width of approximately ¼ inch. Approximately 45% of the surface area of the core was constituted by channels and the remaining 55% of the surface area of the core was not channelled.

Controls A, B, C, D, E, F and G

For purposes of comparison, but not in accordance with the instant invention, several absorbent cores were produced, as described below.

Absorbent core A consisted of embossed cellulose fluff having the same base weight as the cellulose fluff used in Example 1. Core A was embossed with the same diamond pattern as the core of Example 1.

Absorbent core B comprised unembossed cellulose fluff having the same base weight as the fluff used in producing Example 1.

Absorbent core C comprised a layer of the GELOK 6000 DOUBLE PLY/DOUBLE PLY (1080) laminate on top of a cellulose fluff layer. This core differed from Example 1 only in that it was not embossed. This core corresponds with the core of a product that is distributed under the trademark SLIMLINE.

Absorbent core D comprised a layer of embossed cellulose fluff on top of which ARIDALL 1080 polyacrylate super absorbent polymer had been sprinkled. The amount of super absorbent polymer was controlled to provide the same weight thereof, per square inch of the cellulose fluff, as the weight of super absorbent polymer in the GELOK 6000 DOUBLE PLY/DOUBLE PLY (1080) laminate, per square inch thereof.

Absorbent core E comprised a layer of unembossed cellulose fluff on top of which ARIDALL 1080 polyacrylate super absorbent polymer had been sprinkled. The amount of super absorbent polymer was controlled to provide the same weight thereof, per square inch of the cellulose fluff, as the weight of super absorbent polymer in the GELOK 6000 DOUBLE PLY/DOUBLE PLY (1080) laminate, per square inch thereof.

Absorbent core F corresponds with Example 1 except for the embossing pattern. Rather than the diamond shaped embossing pattern, absorbent core F was embossed between smooth upper and lower embossing rollers.

Absorbent core G comprises cellulose fluff which has been split into two layers, between which ARIDALL 1080 polyacrylate super absorbent polymer had been sprinkled. The amount of super absorbent polymer was controlled to provide the same weight thereof, per square inch of the cellulose fluff, as the weight of super absorbent polymer in the GELOK 6000 DOUBLE PLY/DOUBLE PLY (1080) laminate, per square inch thereof.

The absorbent insert of Example 1 and the absorbent cores A–G were tested for absorbency (rate), wicking and skin wetness. The procedure for each test is described below. The results of each test are set forth in Table I.

Absorbency

In this test, a four inch by four inch square sample of absorbent core material, with a water impervious backing, is placed on a level surface. A test plate with a plurality of evenly spaced apertures is placed on the sample. The test plate has sides to retain a test liquid until it passes through the apertures to the absorbent core. The test liquid is a 1.0% NaCl solution. A timer is started after 10.0 milliliters of the test liquid has been introduced into the test plate. The timer is stopped when the test liquid has emptied from the test plate, through the apertures and into the absorbent core. The results of this kind of test are indicative of the rate at which an absorbent product will absorb urine. For example, an absorbent core with a 2 second time in this absorbency test will absorb urine at a faster rate than an absorbent core with a 5 second time in this absorbency test.

Skin Wetness

In this test, a three inch by five inch rectangular sample of absorbent core, with a water impervious backing, is placed on a level surface. In the center of the sample, a 50 milliliter sample of a 1.0% NaCl solution is deposited at the rate of 7.0 milliliters per second. Absorbent paper toweling is cut into three inch by five inch rectangles and a stack of the paper toweling weighing approximately eighteen grams is weighed and its dry weight is recorded. Sixty seconds after the 1.0% NaCl solution has been deposited on the absorbent core sample, a previously weighed stack of paper toweling is placed on top of the absorbent core sample and a three inch by five inch rectangular five pound weight is placed on top of the paper toweling. After fifteen seconds, the weight is removed from the then wet paper toweling which is reweighed. The weight of the dry toweling is subtracted from the weight of the wet paper toweling to give a skin wetness number corresponding with the weight of 1.0% NaCl solution which was released by the absorbent core into the paper toweling. A low number indicates that an absorbent core has good retention of liquid so that adjacent skin will stay relatively dry while a high number indicates that liquid is readily released from an absorbent core so that adjacent skin will become relatively wet.

Wicking

In this test, a seven inch by seven inch square sample of absorbent core, with a water impervious backing, is placed on a level surface. A 25.0 milliliter sample of 1.0% NaCl solution including a blue dye is dispensed from a burette into the center of the sample at the rate of 10.0 milliliters per second. The tip of the burette is ¼ inch from the surface of the absorbent core sample, to prevent spattering of the test liquid. One minute after the test liquid has been dispensed, the perimeter of the wet spot is marked and measurements are taken along a first axis and a second axis which is angularly displaced ninety degrees from the first axis. Thus, the results of this test are expressed in terms of two measurements. A pair of small measurements for an absorbent core indicates that the core does a relatively poor job of distributing or wicking fluid so that fluid may puddle in one area of the absorbent core while the absorptive capacity of remote, dry areas of the absorbent core is wasted. Conversely, a pair of large measurements for an absorbent core indicates that the core does a relatively good job of wicking fluid so that liquid will be well distributed throughout the absorbent core.

TABLE I

| | ABSORBENCY (time in seconds until fully absorbed) | SKIN WETNESS (grams of liquid absorbed by toweling) | WICKING | |
|---|---|---|---|---|
| | | | (side-to side diameter of liquid) | (top to bottom diameter of liquid) |
| EXAMPLE 1 | 2.3 | 12.4 | 5¾" | 6" |
| CORE A | 1.5 | 19.0 | 4" | 4" |
| CORE B | 1.7 | 19.3 | 3½" | 3½" |
| CORE C | 5.5 | 9.0 | 4¼" | 4½" |
| CORE C | 5.0 | — | — | — |
| CORE C* | — | 2.2 | 3½" | 4¼" |
| CORE D | 1.8 | 12.1 | 3½" | 3½" |
| CORE E | 1.4 | 11.3 | 3" | 3¼" |
| CORE F | 1.3 | — | — | — |
| CORE F* | — | 8.4 | 5¾" | 4" |
| CORE G | 2.0 | 14.2 | 3¼" | 2¾" |

(Note: the core identifications which are followed by an asterisk represent absorbent cores which were produced from laminate from a different batch than the laminate which was incorporated in the other absorbent cores for which test results are reported in Table I. As a comparison of the skin wetness numbers for the first and third "Core C" structures suggests, the laminate which was incorporated in the cores marked by an asterisk had a higher concentration of super absorbent polymer than the laminate which was incorporated in the other cores. Accordingly, comparisons between results for cores marked by an asterisk and cores which are not so marked, should take this into account.)

The results set forth in Table I for absorbency demonstrate that unembossed Core C has relatively poor absorbency, while the core of Example 1 has relatively good absorbency. Of the cores that included a layer of laminate, only Core F had a better absorbency number than the Example 1 core. It is theorized that the channel areas in Example 1 promote a rapid absorption of liquid through the laminate layer into the fluff layer. Core F, embossed with flat rollers, simulates the channels in Example 1 and the rapid absorption of liquid into Core F supports the theory that there is very fast absorption through the channels. There is a drawback to the structure of Core F, however, and this is demonstrated by a comparison of Skin Wetness numbers for Core C* and Core F*. Core C* only gave up 2.2 grams of liquid, while Core F* gave up 8.4 grams. This indicates that Core C* with no channels retains liquid much better than Core F* which corresponds with 100% channels. Thus, after 1 minute, liquid can flow back through the laminate, out of Core F*, whereas Core C* with no channels gave up very little liquid in the Skin Wetness test.

The embossing pattern of the Example I core includes a continuous network of channels which exhibits a demonstrated ability to promote good wicking. In fact, Example 1 core had the best wicking numbers although, as indicated in Table I, a direct comparison between Cores C* and F* and the other cores is unwarranted.

Additional samples of cores were separately produced and tested. The additional cores corresponded with the Example I core, Core B and Core C. Some of the cores corresponding with Core C and the Example I core were subjected to the Skin Wetness test described above while others of those cores were subjected to a modified Skin Wetness test in which the toweling and the five pound weight were placed on the specimens ten minutes after wetting, instead of one minute after wetting. The results are set forth below in Table II.

TABLE II

|  | 1 MINUTE SKIN WETNESS (grams) | 10 MINUTE SKIN WETNESS (grams) |
| --- | --- | --- |
| Example I | 6.7 | 3.0 |
| Core C | 3.5 | 1.6 |

The results set forth in Table II demonstrate that the super absorbent polymer continues to absorb liquid after one minute after a wetting. Accordingly, over time, the Skin Wetness performance of the Example I core approaches that of Core C. One minute after wetting, the Example I core gave up 3.2 grams more of liquid than Core C while, ten minutes after wetting, the Example I core gave up only 1.4 grams more of liquid than Core C. These results demonstrate that the Example I core, in addition to exhibiting much better Absorbency than Core C, exhibits Skin Wetness performance which is comparable to Core C, ten minutes after wetting.

An additional set of core samples were separately produced and tested for their ability to absorb multiple wettings. The test procedure corresponded with the Absorbency test procedure outlined above, except that, before the timer is started and ten minutes after the initial wetting, an additional 10 milliliters of liquid was deposited on the core. Then, the timer was started and the time required for the second ten milliliter wetting to be absorbed was recorded. The results of this test, for cores corresponding with Example I, Core B and Core C, are set forth in Table III.

TABLE III

| ABSORBENCY (for a second 10 ml wetting) (seconds) | |
| --- | --- |
| Example I | 19.6 |
| Core B | 6.0 |
| Core C | >120.0 (not all liquid was absorbed after 2 minutes) |

The results set forth in Table III suggest that the channels in the Example I core continue to serve as transfer sites through which liquid can be absorbed, even after an initial wetting. Core C, on the other hand, exhibits an inability to absorb a second wetting. This is believed to be due to "gel-blocking" where swollen, gelled super absorbent polymer particles coalesce to form a layer which blocks additional liquid from being absorbed by the core. Although Core B has excellent Absorbency for a second wetting, Core B cannot hold liquid under pressure, as shown by the data in Table I.

Additional testing has been done on the cores for which data are given in Table I, and on additional cores. The data from this testing for wetness after one minute, wetness after ten minutes, and absorbency for a second wetting are set forth in the following Table IV, below:

TABLE IV

| Type of Core | | Wetness | | Absorbency (for second wetting) |
| --- | --- | --- | --- | --- |
| | | After one Minute | After ten minutes | |
| Example 1 | Gelok 6000 laminate placed on cellulose fluff, and embossed | 6.7 | 3.0 | 19.6 |
| Core B | Unembossed cellulose fluff | 19.3 | 17.3 | 6.0 |
| Core C | Gelok 6000 laminate placed on cellulose fluff, not embossed | 3.5 | 1.6 | >120 |
| Core D | Super absorbent polymer sprinkled onto embossed cellulose fluff | 12.1 | 10.8 | 2.4 |
| Core E | Super absorbent polymer sprinkled onto unembossed cellulose fluff | 11.3 | 8.1 | 8.8 |
| Core H | Super absorbent polymer sprinkled onto cellulose fluff, moistened, heavy tissue placed over moistened | 3.5 | 0.0 | 8.1 |

TABLE IV-continued

| | | Wetness | | |
|---|---|---|---|---|
| Type of Core | | After one Minute | After ten minutes | Absorbency (for second wetting) |
| Core I | polymer, and assembly embossed Super absorbent polymer sprinkled onto cellulose fluff and embossed | 8.3 | 3.0 | 3.8 |
| Brand X | Competitive diaper | 5.4 | 3.7 | 4.2 |

The amount of the super absorbent polymer per square inch of the core was the same in the Example 1 structure and in cores C, D, E and I. There was substantially more of the super absorbent polymer per square inch of Core H, which was produced by apparatus similar to that of FIG. 12 hereof, differing in that it additionally included a dosing wheel 190 from which the super absorbent polymer was deposited onto the fluff, and a picker wheel 198 with picks 202 which formed depressions 206 in the fluff before the super absorbent polymer was deposited thereon (see FIGS. 21 and 22 of U.S. Pat. No. 5,072,687, granted Dec. 17, 1991). Before embossing, the super absorbent polymer was moistened by water sprayed thereon as indicated by dotted lines in FIG. 21 of the patent, and a heavy tissue layer was placed over the moistened polymer. Core H is an example of a core according to the instant invention that is presently being marketed by Principle Business Enterprises.

Figure 7:
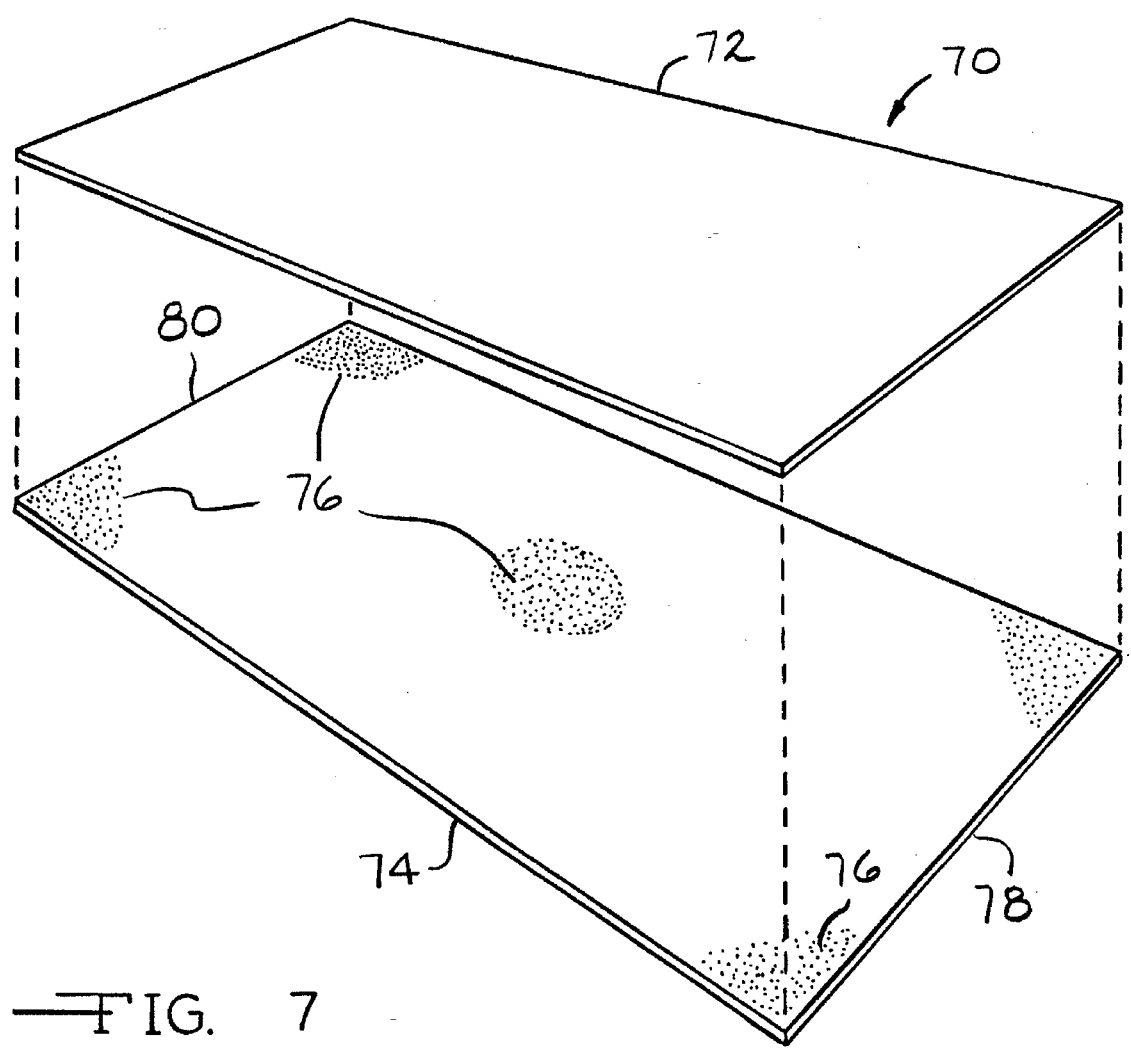
FIG. 7 is an exploded perspective view of the absorptive components of a second embodiment of an absorbent product according to the present invention.
Figure 8:
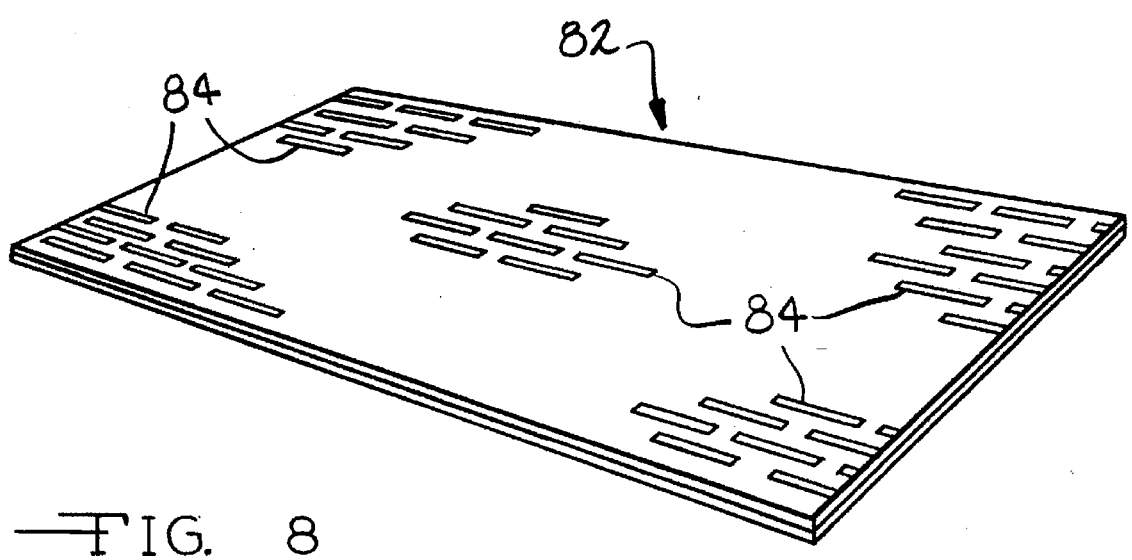
FIG. 8 is a perspective view of the absorptive components illustrated in FIG. 7 after they have been joined together by an embossing operation.

With reference to FIG. 7, the absorptive components of an absorbent product according to a second embodiment of the invention are indicated generally at 70. In this embodiment, the absorptive components 70 comprise an upper layer 72 and a lower layer 74 of thick, air-laid tissue and, on top of the layer 74, a layer of super absorbent polymer particles, represented by dots 76 in the middle and the four corners of the layer 74. The polymer particles can be relatively evenly distributed over the entire layer 74 although the polymer layer need not extend to the reaches of the two ends, 78 and 80 of the layer 74. With the polymer powder in place on the layer 74, the layer 72 is united with the layer 74 and embossed to produce an absorbent core 82, shown in FIG. 8.

A preferred embossing pattern is represented by bars 84 in the middle and the four corners of the core 82. The bars 84 correspond with areas of compression created during the embossing step. Surrounding the bars 84 are uncompressed, tufted areas. The side of the core 82 not illustrated in FIG. 8 has a smooth surface.

Figure 9:
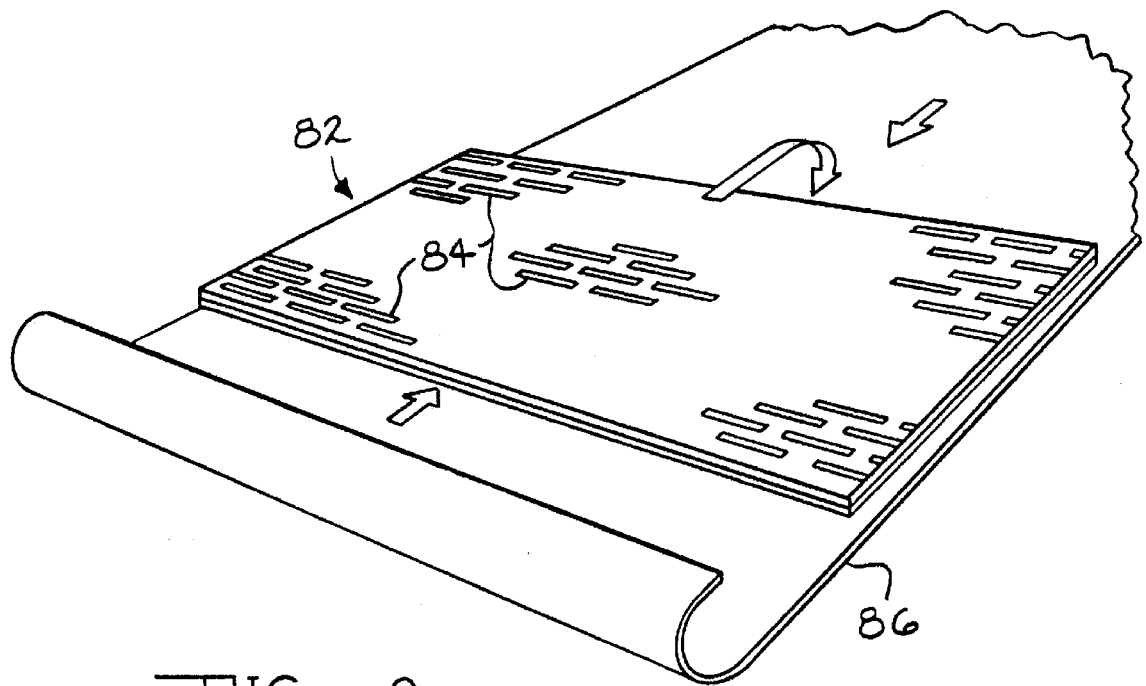
FIG. 9 is a perspective view of a tissue wrapping operation applied to the embossed components illustrated in FIG. 8.
Figure 10:
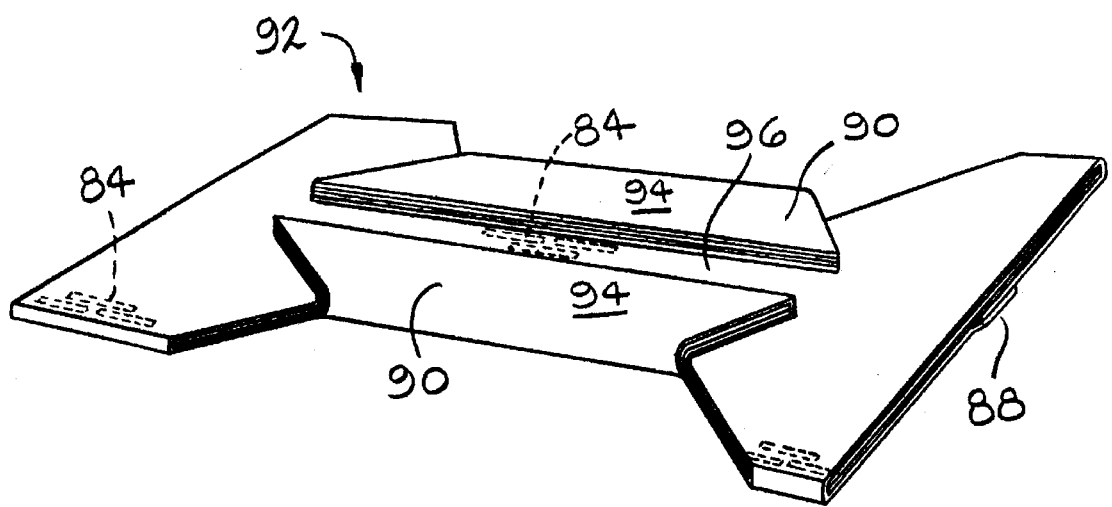
FIG. 10 is a perspective view of the embossed components after a cutting and folding operation.
Figure 11:
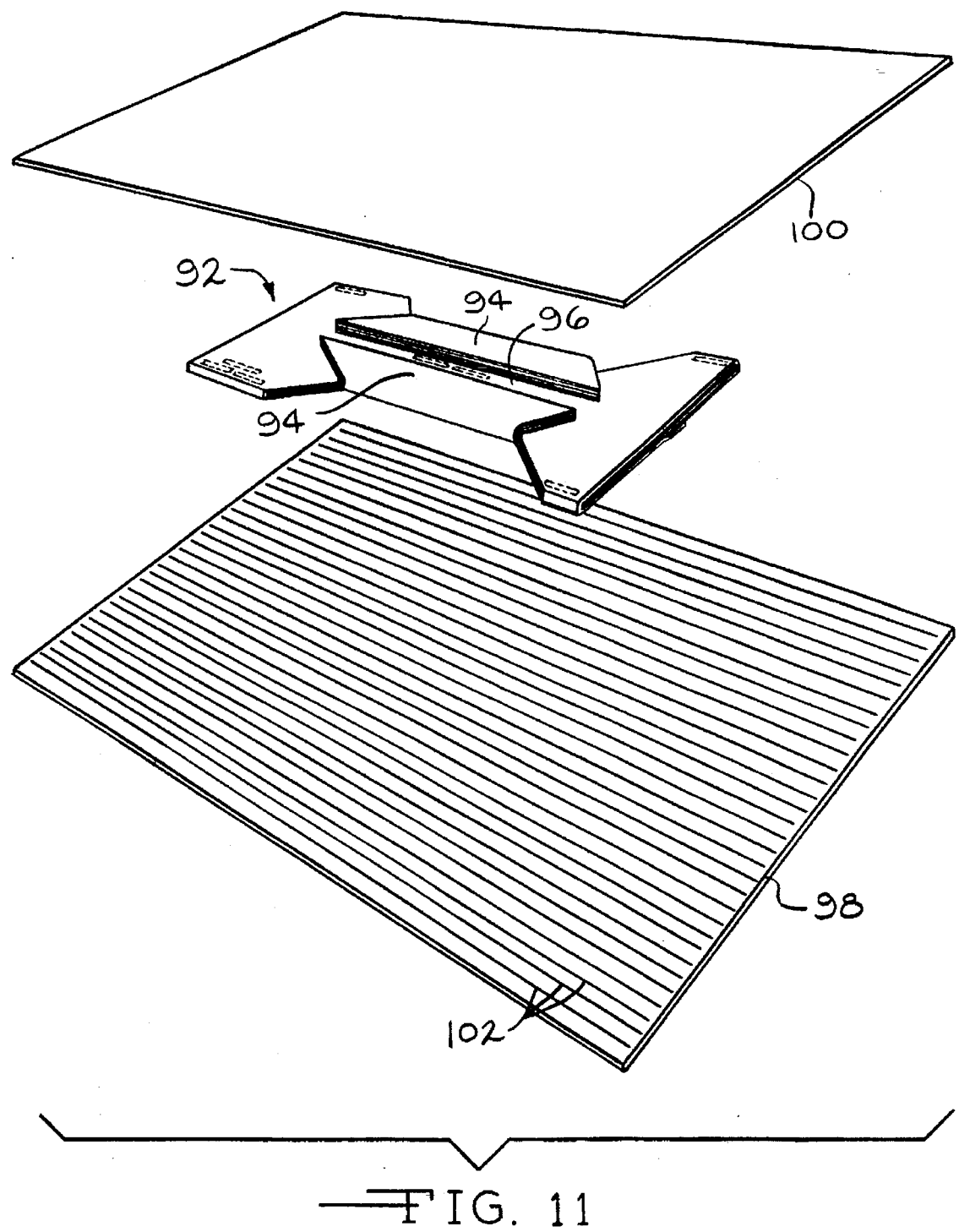
FIG. 11 is an exploded, perspective view of a second embodiment of an absorptive product incorporating the tissue wrapped, embossed absorptive components illustrated in FIG. 10.

With reference to FIG. 9, a tissue wrapping operation is illustrated in which tissue paper 86 is wrapped around the absorbent core 82. When the core 82 is completely wrapped, excess tissue 86 is trimmed and the ends of the wrapped tissue 86 are glued or otherwise secured to produce a seam 88, shown in FIG. 10. The wrapped core 82 is slit to define lateral regions 90 which are folded inwardly, opposite the seam 88, to produce an absorbent insert 92. When the lateral regions are folded inwardly, a smooth surface 92 is exposed. The slitting and folding steps are controlled so that a substantial gap remains between the edges of the lateral regions 90 to define a central region 94. The exposed surface in the central region 94 includes compressed areas represented by the bars 84. An absorbent article can be produced from the absorbent insert 92, by sandwiching it between a water impervious backing sheet 98 and a non-woven facing sheet 100. Lines 102 of hot melt adhesive are applied to the backing sheet 98 to adhesively secure it to the absorbent insert 92 and the facing sheet 100. If desired, elastic means (not shown) corresponding with the means 46 (FIG. 5) can be applied to the backing sheet 98 (FIG. 11) to produce gathers in a finished absorbent product.

After the insert 92 has been assembled between the backing sheet 98 and the facing sheet 100, leg cut outs would be trimmed from the assembly, as discussed above with reference to FIG. 6.

Figure 12:
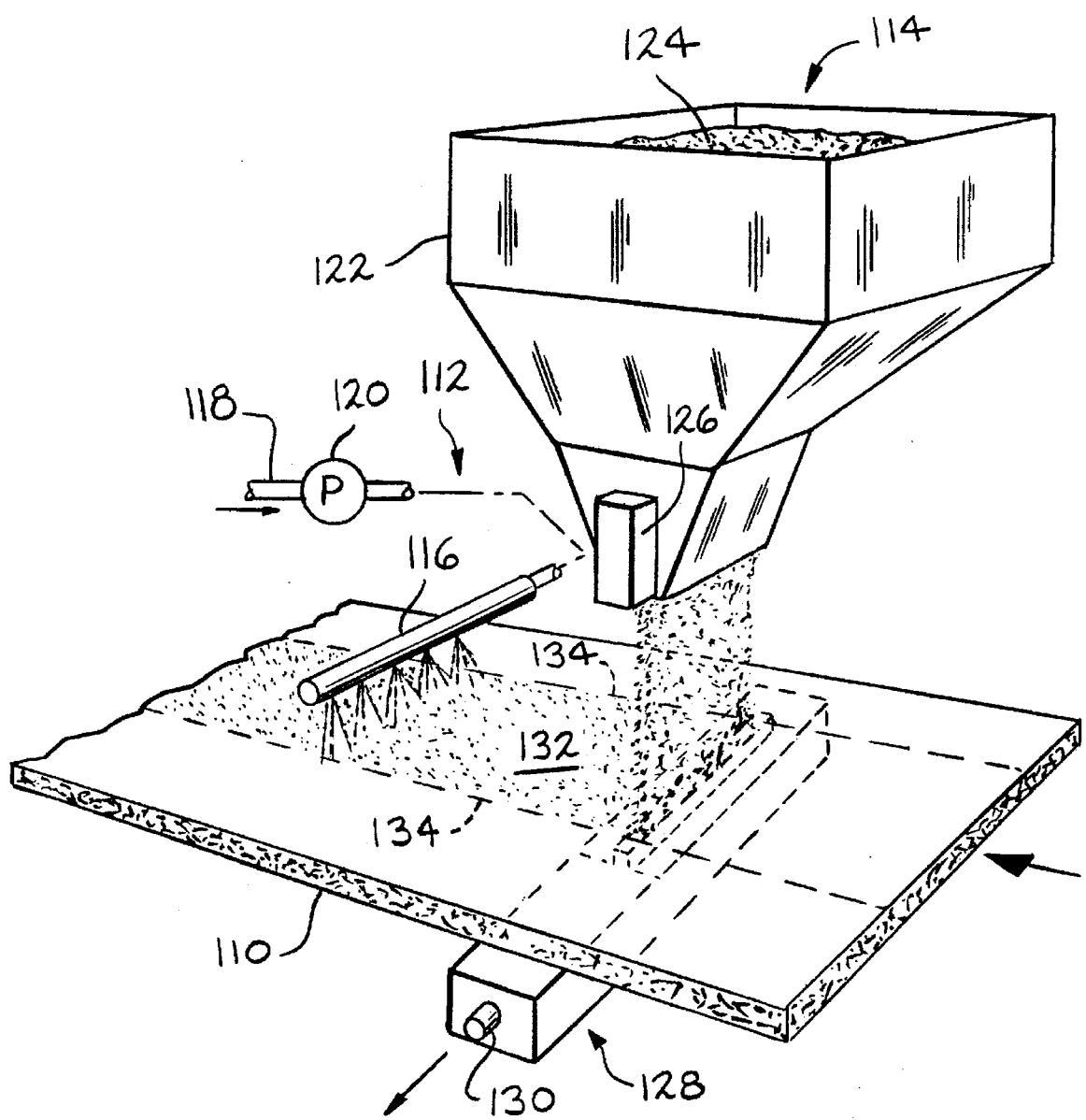
FIG. 12 is a perspective view of apparatus for depositing polymer to produce one of the absorptive components of third and fourth embodiments of an absorbent product according to the present invention.

Referring now to FIG. 12, the direct deposition of a super absorbent polymer onto a fluff layer 110 will now be described. Layer 110 is a relatively thick layer of moisture absorbing material, such as cellulose fluff, fluffed wood pulp, batting or the like.

Apparatus for use in depositing polymer powder on the fluff layer 110 comprises water spray means indicated generally at 112 and polymer deposition means indicated generally at 114. The water spray means comprises a spray head 116 to which water is supplied through conduit 118 at a constant pressure which may be monitored or controlled by a pressure controller 120. The polymer deposition means 114 comprises a trough 122 for holding polymer powder, indicated at 124, and deposition rate control means 126 for adjusting the rate at which polymer powder 124 is released from the trough 122. Beneath the polymer deposition means 114, specifically, the trough 122, there is provided a vacuum integration means 128 for drawing a vacuum below the fluff layer to draw polymer powder 124 into the fluff layer where the fluff fibers will engage and retain it. A central conduit 130 in the vacuum integration means 128 can be connected to a suitable vacuum source (not shown).

Figure 13:
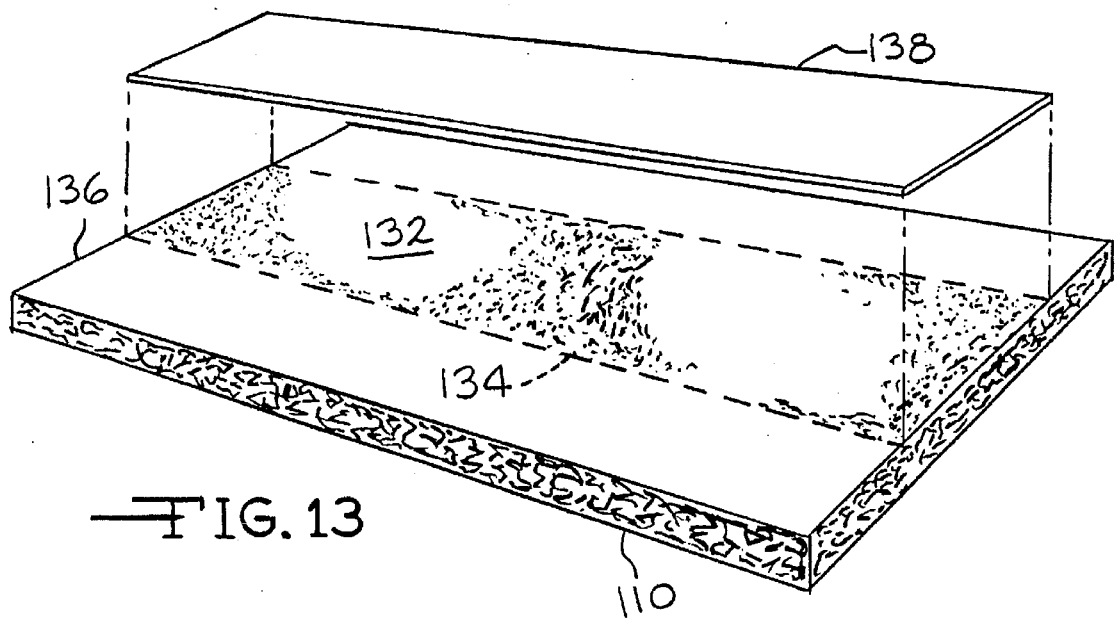
FIG. 13 is a perspective view of absorbent components of a third embodiment of the invention, including a component produced on the apparatus illustrated in FIG. 12.

The water spray means 112 and the polymer deposition means 114 are positioned and sized to spray water and deposit polymer powder on the fluff layer 110 in a central region 132 defined between dotted lines 134. The polymer deposition means 114 may be operated continuously, or intermittently so that discreet absorbent portions of the central region 132 having polymer powder 124 deposited thereon are separated by discreet portions of the central region 132 which do not have polymer powder 114 deposited thereon. Continuous operation of the polymer deposition means 114 will produce a continuous layer of polymer powder 124 in the central region 132 of a piece 136 which has been cut from the fluff layer 110, as shown in FIG. 13. Intermittent deposition of polymer powder 124 could be used to produce a piece, like the piece 136, except that the polymer powder 124 would not extend all of the way to the edges; it would be recessed from all four sides of the piece.

During operation of the FIG. 12 apparatus, fluff material constituting the layer 110 is advanced from right to left, passing first under the polymer deposition means 114 and then under the water spray means 112. By controlling the rate of deposition of polymer powder 124, relative to the rate at which the fluff layer is advanced, one can achieve a desired concentration of polymer powder in the fluff material 110. In the central region, a concentration of approximately 130 grams of polymer (ARIDALL 1080 polyacrylate super absorbent polymer) per square meter is a good concentration. More or less polymer may be used, depending on a number of factors including the identity and capacity of the super absorbent polymer and the intended use.

After the polymer powder 124 is deposited in the central region 132 of the layer 110, water or an aqueous solution of a water soluble adhesive is sprayed on the central region. The water or the like promotes bonding between the fibers constituting the layer 110 and the polymer powder. Additionally the water or the like plays an important role during an embossing operation which is described below.

Figure 14:
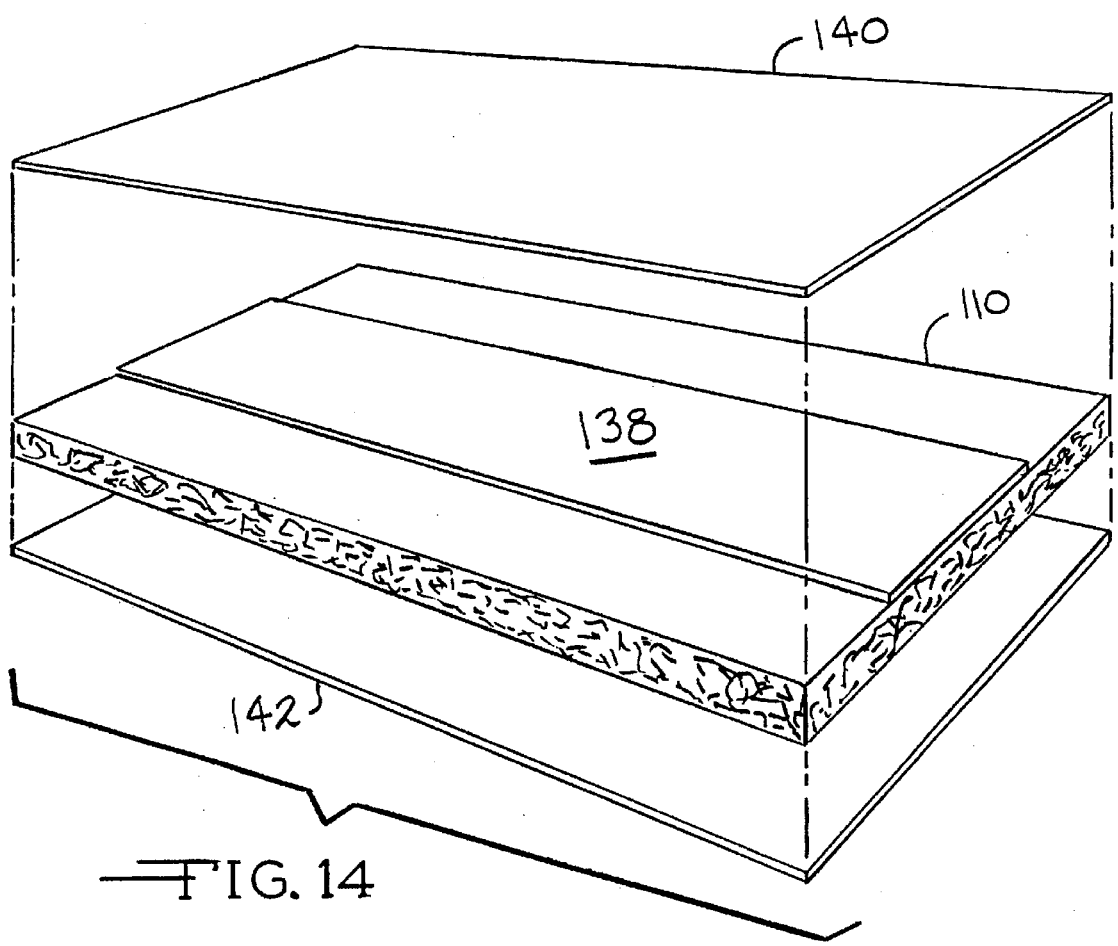
FIG. 14 is an exploded, perspective view of the absorptive components illustrated in FIG. 13, and upper and lower tissue layers.

With further reference to FIG. 13, there is illustrated a layer 138 of heavy tissue, corresponding in size with the central region 132. As illustrated in FIG. 14, the tissue layer 138 is positioned on the piece 136 so that it covers the central region 132 and the polymer powder 124 deposited thereon. The layer 138 is positioned on the same side of the fluff layer 110 as that on which the polymer powder 124 was deposited. The layer 138, as well as the layer 24 (FIG. 1) can be single ply or double ply. If single ply, the tissue should have a basis weight of between 14 pounds and 18 pounds. If double ply, the tissue should have a basis weight of between 14 pounds and 22 pounds. A single ply tissue with a basis weight of 14.5 pounds produces very good results. The tissue layers 138 and 24 (FIG. 1) should consist of a tissue with good stretchability; 18% to 33% machine direction stretch is preferred.

In FIG. 14, upper and lower tissue layers 140 and 142 are positioned to be brought into contact with the upper and lower surfaces of the piece 136. The tissue layers 140 and 142 are light by comparison with the tissue layer 138. A 12 pound basis weight wet strength tissue is preferred for the layers 140 and 142 as well as for the layers 28 and 30 (FIG. 2) and the tissue wrap 86 (FIG. 9).

Figure 15:
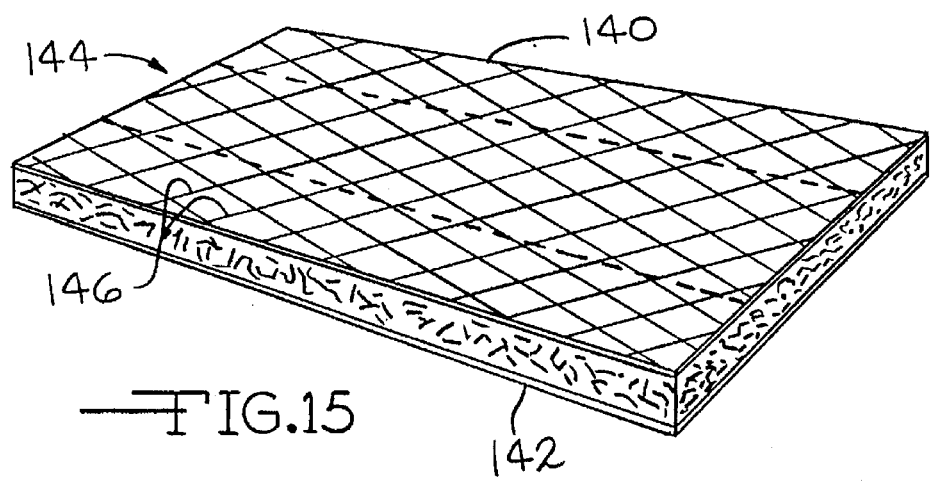
FIG. 15 is a perspective view of an absorbent core comprising the components illustrated in FIG. 14, after they have been integrated by an embossing operation.

After the tissue layers 140 and 142 are brought into contact with the piece 136, the components are subjected to an embossing step. A smooth roller (not shown) is applied to the lower tissue layer 142 and a patterned roller (not shown) is applied to the opposed, upper tissue layer 140 to produce an embossed absorbent core 144. A suitable diamond embossing pattern is shown in FIG. 15, reflected in the pattern shown on the surface of the tissue layer 140. The embossing pattern on the embossing die (not shown) applied to the upper tissue layer 140 produces a pattern of channels 146 in the tissue layer 140, the tissue layer 138, and the fluff layer 110. As is explained above, these channels 146 constitute transfer sites through which liquid is absorbed quickly from above the upper tissue layer 140, through the tissue layer 138, to the fluff layer 110 where it will be absorbed, eventually by the polymer powder 124 dispersed therein. The channels 146 are interconnected in a continuous network which promotes excellent wicking characteristics.

In the channels 146, there is a high density interface between the tissue layers 138 and 140 and the fluff layer 110. In this interface, there is a physical bond between the layers 138, 140 and 110 which gives the absorbent core 144 physical integrity. In the areas between the channels 146, the layers 138, 140 and 110 have a lower density than these layers have in the channels 146. The polymer powder 124 is, in effect, laminated between the tissue layer 138 and the fluff layer 110. This core construction is advantageous because migration of the powder 124 is resisted while swelling of the powder 124 is relatively unrestricted. The channels 146 promote fast absorption. This core construction also provides very high capacity with an ability to absorb multiple wettings. These characteristics are believed to be due, in part, to what amounts to a three dimensional distribution of polymer powder in the core 144, as opposed to a two dimensional distribution of polymer powder in absorbent products which include a super absorbent polymer laminated between two tissue layers. In the former, there is a degree of freedom for the polymer to expand into the fluff layer whereas, in the latter, the polymer is stuck between two tissue layers in a substantially two-dimensional plane. For example, Core C is an absorbent core which included a super absorbent laminate with super absorbent polymer sandwiched between tissue layers. As the results set forth in TABLE III indicate, core C could not absorb a second wetting, even after two minutes. It appeared that the super absorbent polymer in the laminate layer in Core C had expanded and coalesced to form a two-dimensional barrier layer through which liquid could not pass. In contrast, the super absorbent polymer in the core 144 is not confined in a two-dimensional plane. Consequently, the core 144 can absorb multiple wettings. The core 144 has good skin wetness performance, i.e., it retains fluid well, even under pressure. It is believed that the three-dimensional distribution of super absorbent polymer in this core construction allows the polymer to have greater capacity because there is more room for the polymer to expand. Once liquid is taken up by the super absorbent polymer, the liquid is not released, even under pressure. Liquid that is not picked up by the polymer will be held in the fluff layer. Although liquid can be squeezed out of fluff, this core construction resists the squeeze out of liquid, back through the upper tissue layer 140. The polymer powder in the core 144 is concentrated on and near the upper surface of the fluff layer 110. When the absorbent core is not under pressure, the polymer is distributed in three-dimensions, as discussed above. However, when the core is compressed after a wetting, the gelled, swollen polymer particles will be brought into close contact forming a barrier layer to prevent the squeeze out of liquid through the upper tissue layer 140.

The embossing step can be carried out advantageously with approximately 50 to 175 lbs of pressure per lineal inch of the embossing rollers. A variety of patterns would be suitable for the patterned embossing roller, beside the one reflected in the upper tissue layer 140 shown in FIG. 15.

It will be appreciated that the manufacturing steps described above with reference to FIGS. 12–15 can be applied to bulk materials supplied, for example, from rolls. Specifically, the fluff layer 110, the tissue layers 138, 140 and 142 can be manufactured into an embossed, absorbent core 144 of infinite length which can later be cut to appropriate length and incorporated into an absorbent product according to the instant invention. After the absorbent core 144 has been embossed, it is preferably subjected to a de-bulking operation in which it is passed between two compression rollers (not shown). This step adds further integrity to the embossed absorbent core 144 and promotes more economical packaging by producing thinner absorbent products.

Figure 16:
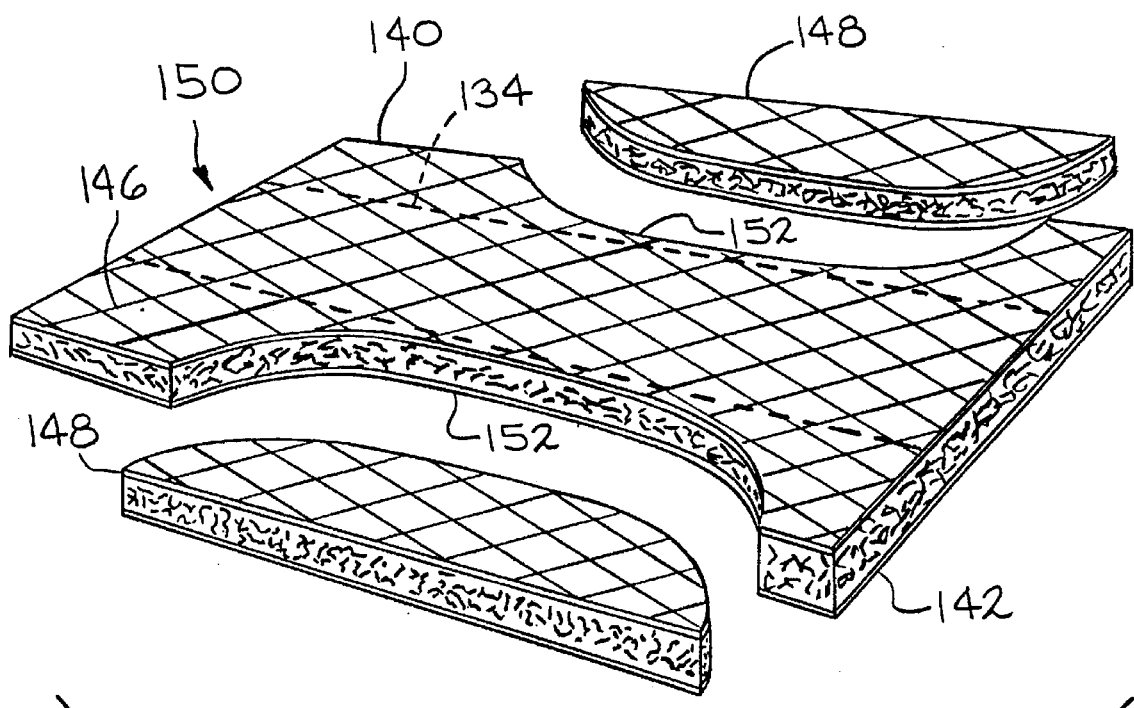
FIG. 16 is a perspective view of the absorbent core during a trimming operation.

Referring now to FIG. 16, the embossed absorbent core 144 is illustrated after ears 148 have been trimmed therefrom to produce an absorbent insert 150, with leg cut outs 152, for incorporation in an absorbent product. The cut outs 152 extend inwardly toward, but terminate just short of, the central region 132 defined between the dotted lines 134. The ears 148 can be recycled, if desired, to yield material suitable for producing additional fluff layers 110. The trimming can be carried out with a die-cutter which may include a cutter for cutting the embossed absorbent core 144 to produce an absorbent insert 150 of a given length. Alternatively, a separate cutter may be used to cut absorbent core material to an appropriate length.

As used hereinabove, the term fluff refers to a web made up of loose fibers. It is also intended to encompass composite webs made up of such fibers and including other materials such as synthetic fibers. For example, Hercules distributes, under the name Pulpex, a polyethylene/polypropylene blend of fibers which can be advantageously incorporated into a fluff layer. Pulpex, in amounts of five percent can be incorporated into fluff and heated to improve the integrity of the fluff layer.

Figure 17:
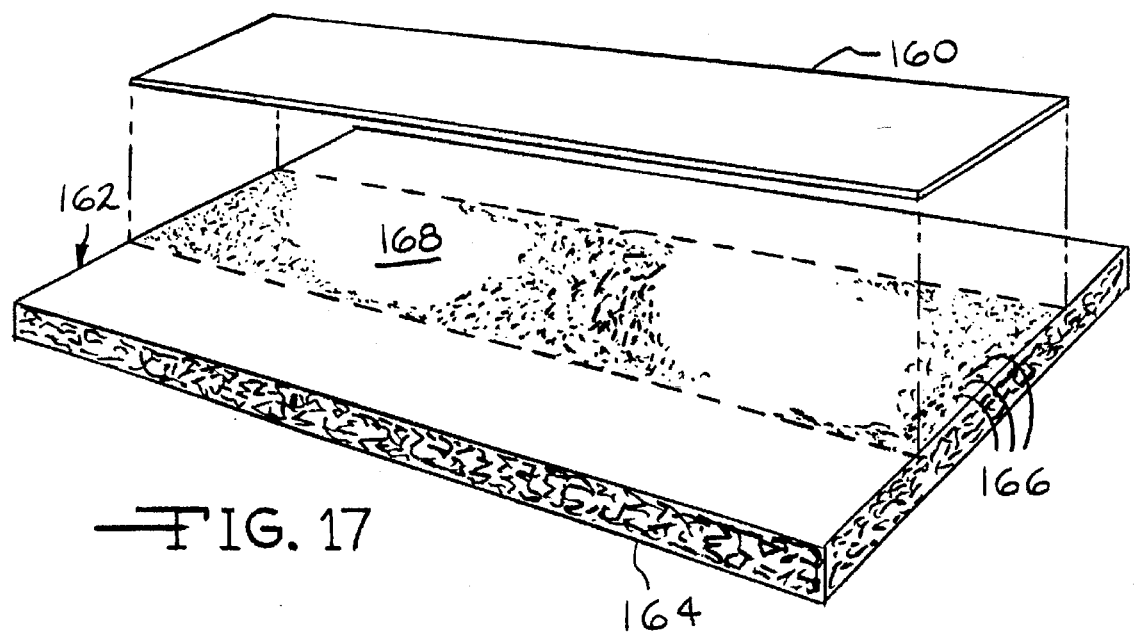
FIG. 17 is a perspective view of absorbent components of a fourth embodiment of the invention, including a component produced on the apparatus illustrated in FIG. 12.

With reference to FIG. 17, another embodiment of an absorbent core comprises a layer 160 of laminate and piece 162 consisting of a fluff layer 164 and super absorbent polymer powder 166 deposited in a central region 168 of the fluff layer 164. The piece 162 can be readily produced on apparatus of the type described above with reference to FIG. 12. It will be appreciated that the apparatus of FIG. 12 can be operated so that it intermittently deposits polymer powder 166 on the central region 168 of the layer of fluff 164. In that case, the layer of polymer powder 166 would terminate short of the ends of the piece 162, as well as terminating short of the sides of the piece 162, as shown in FIG. 17.

Figure 18:
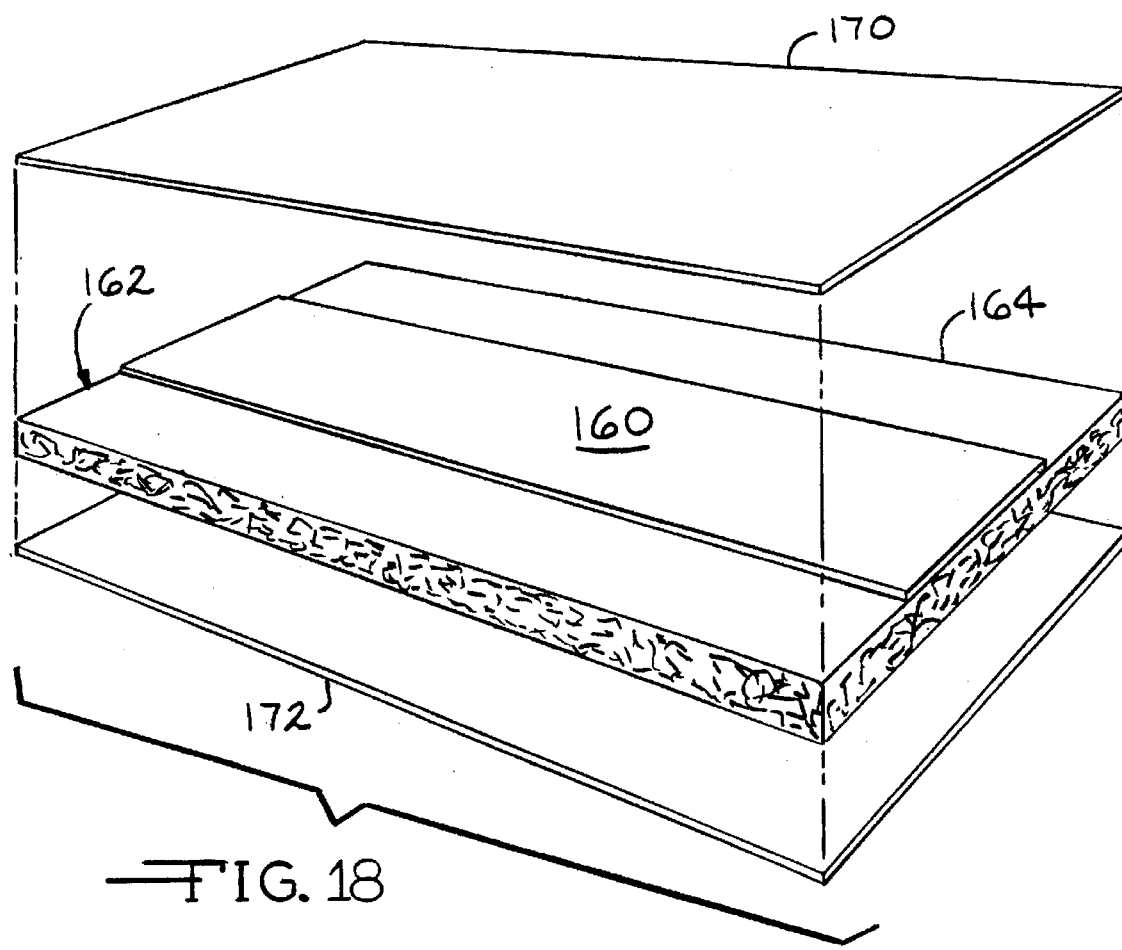
FIG. 18 is an exploded, perspective view of the absorptive components illustrated in FIG. 17, and upper and lower tissue layers.

The laminate layer 160 comprises super absorbent polymer powder dispersed in and supported on a heavy tissue. Preferable, the layer 160 of laminate is GELOK 6000 SINGLE PLY/DOUBLE PLY, a laminate consisting of 1080 polyacrylate super absorbent polymer sandwiched between a single ply of 14 pound basis weight tissue and two sheets of 10.5 pound basis weight tissue. The laminate layer corresponds in size with the central region 168 where the polymer powder 166 is deposited. As illustrated in FIG. 18, the laminate layer 160 is positioned on the piece 162 so that it covers the central region 168 and the polymer powder 166 deposited thereon. The laminate layer 160 is positioned on the same side of the fluff layer 164 as that on which the polymer powder 166 was deposited. The laminate layer can be single ply or double ply. If single ply, the tissue should have a basis weight of between 14 pounds and 18 pounds. If double ply, the tissue should have a basis weight of between 14 pounds and 22 pounds. A single ply tissue with a basis weight of 14.5 pounds produces very good results. The laminate layer 160 should consist of a tissue with good stretchability; 18% to 33% machine direction stretch is preferred.

In FIG. 18, upper and lower tissue layers 170 and 172 are positioned to be brought into contact with the upper and lower surfaces of the piece 162. Optionally, a single ply of heavy tissue (not shown) can be positioned between the piece 162 and the tissue layer 170. The tissue layers 170 and 172 are light by comparison with the tissue incorporated into the laminate layer 160. A 12 pound basis weight wet strength tissue is preferred for the layers 170 and 172.

Figure 19:
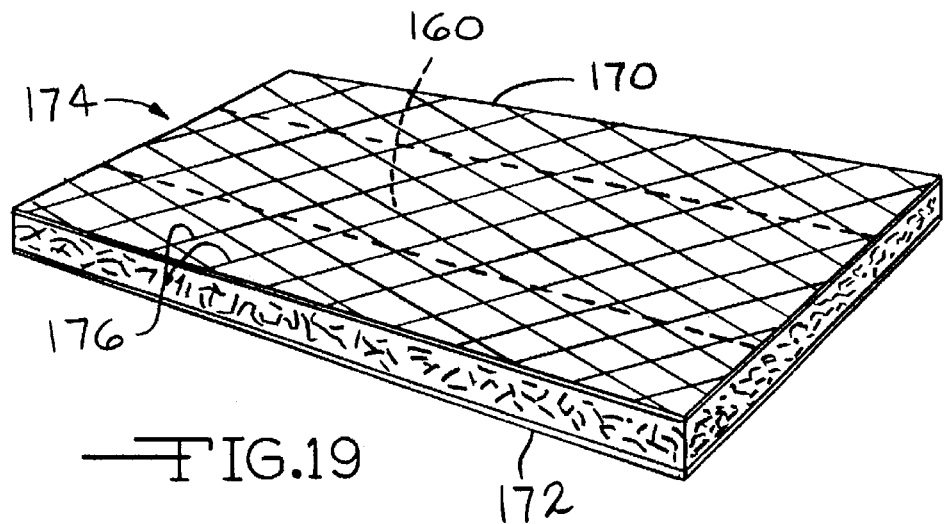
FIG. 19 is a perspective view of an absorbent core comprising the components illustrated in FIG. 18, after they have been integrated by an embossing operation.

After the tissue layers 170 and 172 are brought into contact with the piece 162, the components are subjected to an embossing step. A smooth roller (not shown) is applied to the lower tissue layer 172 and a patterned roller (not shown) is applied to the opposed, upper tissue layer 170 to produce an embossed absorbent core 174 shown in FIG. 19. A suitable diamond embossing pattern is shown in FIG. 19, reflected in the pattern shown on the surface of the tissue layer 170. The embossing pattern on the embossing die (not shown) applied to the upper tissue layer 170 produces a pattern of channels 176 in the tissue layer 170, the laminate layer 160, and the fluff layer 164. These channels 176 constitute transfer sites through which liquid is absorbed quickly from above the upper tissue layer 170, through the laminate layer 160, to the fluff layer 164 where it will be absorbed, eventually by the polymer powder 166 dispersed therein. The channels 176 are interconnected in a continuous network which promotes excellent wicking of deposited fluid, through the channels, to portions of the embossed absorbent core 174 remote from the deposit site. The polymer powder which is deposited in the fluff layer locks in liquid which is absorbed throughout the channels 176 to yield excellent skin dryness characteristics for the absorbent core 174, while the channels 176 provide excellent absorbency characteristics. Moreover, as demonstrated in Table III, an absorbent core (Example I) which has been embossed to provide channels, can absorb multiple wettings.

In the channels 176, there is a high density interface between the laminate layer 160, the tissue layer 170 and the fluff layer 164. In this interface, there is a physical bond between the layers 160, 170 and 164 which gives the absorbent core 174 physical integrity. In the areas between the channels 176, the layers 160, 170 and 164 have a lower density than these layers have in the channels 176. The polymer powder 166 that has been deposited on the fluff layer 164 is, in effect, laminated between the laminate layer 160 and the fluff layer 164. This core construction is advantageous because migration of the deposited powder 166 is resisted while swelling of the deposited powder 166 is relatively unrestricted. The channels 176 provide the absorbent insert with excellent absorbency. This core construction also provides very high capacity with an ability to absorb multiple wettings. These characteristics are believed to be due, in part, to what amounts to a three dimensional distribution of polymer powder in the core 144, as opposed to a two dimensional distribution of polymer powder in absorbent products which include a super absorbent polymer laminated between two tissue layers. Thus, the absorbent core 174 combines the high capacity afforded by super absorbent polymer dispersed in fluff with the excellent skin wetness and core integrity afforded by the embossed laminate/fluff structure.

The embossing step can be carried out advantageously with approximately 50 to 175 lbs of pressure per lineal inch of the embossing rollers. A variety of patterns would be suitable for the patterned embossing roller, beside the one reflected in the upper tissue layer 170 shown in FIG. 19.

It will be appreciated that the manufacturing steps described above with reference to FIGS. 17–19 can be applied to bulk materials supplied, for example, from rolls. Specifically, the fluff layer 164, the laminate layer 160, the tissue layers 170 and 172 can be manufactured into an embossed, absorbent core 174 of infinite length which can later be cut to appropriate length and incorporated into an absorbent product according to the instant invention. After the absorbent core 174 has been embossed, it is preferably subjected to a de-bulking operation in which it is passed between two compression rollers (not shown). This step adds further integrity to the embossed absorbent core 174 and promotes more economical packaging by producing thinner absorbent products.

Figure 20:
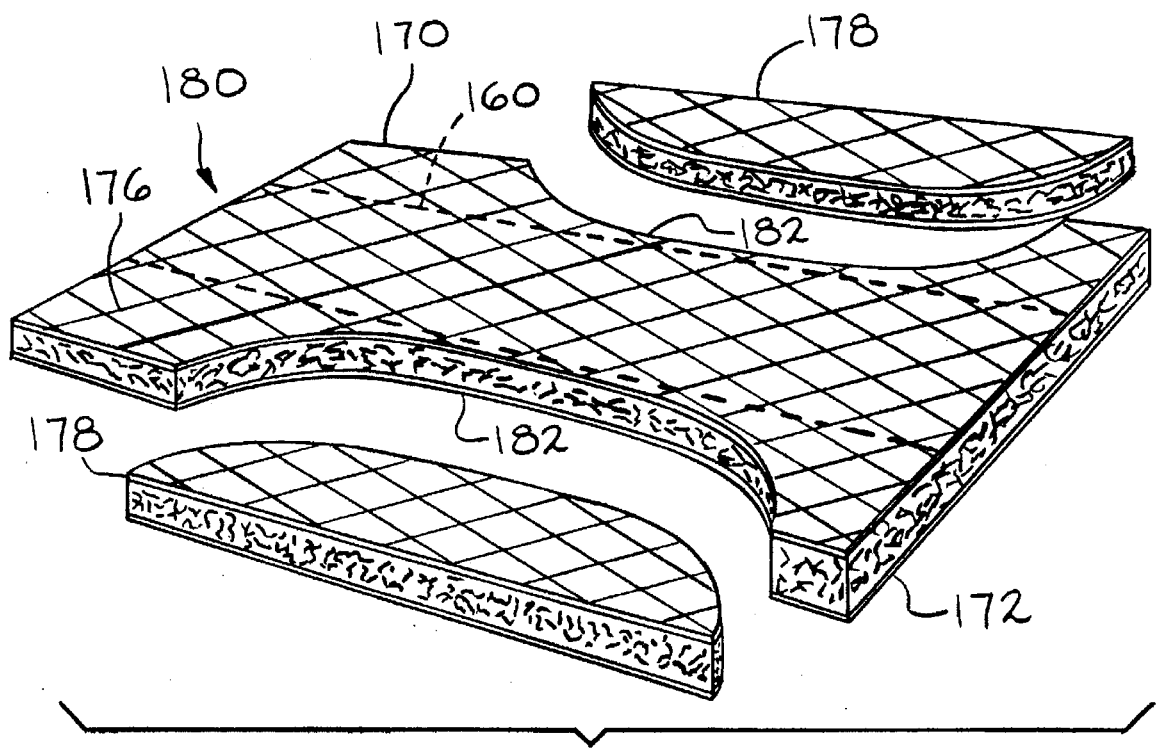
FIG. 20 is a perspective view of the absorbent core during a trimming operation.

Referring now to FIG. 20, the embossed absorbent core 174 is illustrated after ears 178 have been trimmed therefrom to produce an absorbent insert 180, with leg cut outs 182, for incorporation in an absorbent product. The cut outs 182 extend inwardly toward, but terminate just short of, the layer 160 of laminate. The ears 178 can be recycled, if desired, to yield material suitable for producing additional fluff layers 164. The trimming can be carried out with a die-cutter which may include a cutter for cutting the embossed absorbent core 174 to produce an absorbent insert 180 of a given length. Alternatively, a separate cutter may be used to cut absorbent core material to an appropriate length.

The absorbent inserts 150 and 180 can readily be incorporated in a diaper product such as the absorbent product 54 shown in FIG. 6. Alternatively, these inserts can be sandwiched between a layer of non-woven material and poly backing to produce pad products, such as a bed pad, without leg cut outs 56 as provided for the absorbent product 54.

The foregoing description is intended to enable those skilled in the art to practice the present invention and constitutes the best mode presently known for practicing the invention. Undoubtedly, modifications will occur to those skilled in the art, and such modifications may be resorted to without departing from the spirit and scope of the invention disclosed herein and claimed below.

We claim:

1. An absorbent core including a given amount of a super absorbent polymer, said core consisting essentially of
   a water permeable cover sheet,
   an absorbent fluff layer having first and second major surfaces, said first surface being positioned adjacent to said cover sheet,
   an absorbent laminate layer for absorbing and retaining liquid, said absorbent laminate layer
   (a) being positioned between said fluff layer and said cover sheet,
   (b) consisting essentially of aperture free tissue and a first portion of super absorbent polymer that is subject to gel blocking when wet, and is present in an amount sufficiently great that gel blocking occurs when the laminate is wet, said first portion of super absorbent polymer being less than the given amount, and being secured to and supported on said tissue, and
   (c) being positioned so that it is adjacent to and covers at least a central portion of the first major surface of said fluff layer, a second portion of super absorbent polymer distributed in said fluff layer, adjacent to the first major surface thereof,
   wherein said fluff layer and said absorbent laminate layer are connected to each other by a plurality of channel regions consisting of compressed, physically integrated portions of said fluff layer and of said absorbent laminate layer, the channel regions having a given density and, between the channel regions, discrete regions composed of portions of said fluff layer and of said absorbent laminate layer, and having a density less than the given density, said channel regions having been formed by pressing absorbent laminate into a moistened surface of said fluff layer, and the absorbent core has improved absorbency as a consequence of said channel regions, and is operable to absorb, through said cover sheet, multiple wettings with simulated urine in quantities which would cause gel blocking in the absence of said channel regions.

2. The absorbent core claimed in claim 1 in which the second major surface of said fluff layer is substantially smooth, while the channel regions in the physically integrated portions of said fluff layer and said absorbent laminate layer are diamond shaped.

3. The absorbent core claimed in claim 1 wherein the channel regions are arranged in a repeating diamond shaped pattern.

4. An absorbent product consisting essentially of an absorbent core including a given amount of a super absorbent polymer, said core consisting essentially of a water permeable cover sheet,
   an absorbent fluff layer having first and second major surfaces, said first surface being positioned adjacent to said cover sheet,
   an absorbent laminate layer for absorbing and retaining liquid, said absorbent laminate layer
   (a) being positioned between said fluff layer and said cover sheet,
   (b) consisting essentially of aperture free tissue and a first portion of super absorbent polymer that is subject to gel blocking when wet, and is present in an amount sufficiently great that gel blocking occurs when the laminate is wet, said first portion of super absorbent polymer being less than the given amount, and being secured to and supported on said tissue, and
   (c) being positioned so that it is adjacent to and covers at least a central portion of the first major surface of said fluff layer,
   a second portion of super absorbent polymer distributed in said fluff layer, adjacent to the first major surface thereof,
   wherein said fluff layer and said absorbent laminate layer are connected to each other by a plurality of channel regions consisting of compressed, physically integrated portions of said fluff layer and of said absorbent laminate layer, the channel regions having a given density and, between the channel regions, discrete regions composed of portions of said fluff layer and of said absorbent laminate layer, and having a density less than the given density, said channel regions having been formed by pressing absorbent laminate into a moistened surface of said fluff layer, and the absorbent core has improved absorbency as a consequence of said channel regions, and is operable to absorb, through said cover sheet, multiple wettings with simulated urine in quantities which would cause gel blocking in the absence of said channel regions, and
   a water impervious backing sheet positioned adjacent the second surface of said absorbent fluff layer.

5. The absorbent product of claim 4 wherein said absorbent core further comprises a tissue sheet which is positioned between said fluff layer and said backing sheet.

6. An absorbent core including a super absorbent polymer, said core consisting essentially of
   a water permeable cover sheet,
   an absorbent fluff layer having first and second major surfaces, the first surface being positioned adjacent to said cover sheet,
   a layer of tissue disposed between the first major face of said fluff layer and said cover sheet, and
   super absorbent polymer powder distributed in said fluff layer, adjacent to the first major surface,
   wherein said fluff and tissue layers are connected to each other by a plurality of channel regions consisting of compressed, physically integrated portions of the fluff and tissue layers having a given density and, between the channel regions, discrete regions of portions of said fluff and tissue layers having a density less than the given density, said channel regions having been formed by pressing the tissue layer into a moistened surface of the fluff layer, and the absorbent core has improved absorbency as a consequence of said channel regions, and is operable to absorb, through said cover sheet, multiple wettings with simulated urine in quantities which would cause gel blocking in the absence of said channel regions.

7. The absorbent core claimed in claim 6 in which the second major surface of said fluff layer is substantially smooth, while the channel regions in the physically integrated portions of said fluff layer and said absorbent laminate layer are diamond shaped.

8. The absorbent core claimed in claim 6 wherein the channel regions are arranged in a repeating diamond shaped pattern.

9. An absorbent product consisting essentially of an absorbent core including a super absorbent polymer, said core consisting essentially of a water permeable cover sheet, an absorbent fluff layer having first and second major surfaces, the first surface being positioned adjacent to said cover sheet, a layer of tissue disposed between the first major surface of said fluff layer and said cover sheet, and super absorbent polymer powder distributed in said fluff layer, adjacent to the first major surface, wherein said fluff and tissue layers are connected to each other by a plurality of channel regions consisting of compressed, physically integrated portions of the fluff and tissue layers having a given density and, between the channel regions, discrete regions of portions of said fluff and tissue layers having a density less than the given density, said channel regions having been formed by pressing the tissue layer into a moistened surface of the fluff layer, and the absorbent core has improved absorbency as a consequence of said channel regions, and is operable to absorb, through said cover sheet, multiple wettings with simulated urine in quantities which would cause gel blocking in the absence of said channel regions, and a water impervious backing sheet positioned adjacent the second surface of said absorbent fluff layer.

10. The absorbent product of claim 9 wherein said absorbent core further comprises first and second tissue sheets, said first tissue sheet being positioned between said fluff layer and said backing sheet, said second tissue sheet being positioned between said absorbent laminate layer and said cover sheet, and said second tissue sheet being integrated by the pressing operation into the higher density channel regions of the absorbent core.

11. An absorbent core consisting essentially of a water permeable cover sheet, an absorbent fluff layer having first and second major surfaces, said first surface being positioned adjacent to said cover sheet, an absorbent laminate layer for absorbing and retaining liquid, said absorbent laminate layer (a) being positioned between said fluff layer and said cover sheet, (b) consisting essentially of aperture free tissue and a super absorbent polymer that is subject to gel blocking when wet, and is present in an amount sufficiently great that gel blocking occurs when the laminate is wet, said super absorbent polymer being secured to and supported on said tissue, and (c) being positioned so that it is adjacent to and covers at least a central portion of said first major surface of said fluff layer, wherein said first layer and said absorbent laminate layer are connected to each other by a plurality of channel regions consisting of compressed, physically integrated portions of said fluff layer and of said absorbent laminate layer, the channel regions having a given density and, between the channel regions, discrete regions composed of portions of said fluff layer and of said absorbent laminate layer having a density less than the given density, said channel regions having been formed by pressing absorbent laminate into a moistened surface of the fluff layer, and the absorbent core has improved absorbency as a consequence of said channel regions, and is operable to absorb, through said cover sheet, multiple wettings with simulated urine in quantities which would cause gel blocking in the absence of said channel regions.

12. The absorbent core claimed in claim 11 in which the second major surface of said fluff layer is substantially smooth, while the channel regions in the physically integrated portions of said fluff layer and of said absorbent laminate are diamond shaped.

13. The absorbent core claimed in claim 11 wherein the channel regions are arranged in a repeating diamond shaped pattern.

14. An absorbent product consisting essentially of an absorbent core consisting essentially of a water permeable cover sheet, an absorbent fluff layer having first and second major surfaces, said first surface being positioned adjacent to said cover sheet, an absorbent laminate layer for absorbing and retaining liquid, said absorbent laminate layer (a) being positioned between said fluff layer and said cover sheet, (b) consisting essentially of aperture free tissue and a super absorbent polymer that is subject to gel blocking when wet, and is present in an amount sufficiently great that gel blocking occurs when the laminate is wet, said super absorbent polymer being secured to and supported on said tissue, and (c) being positioned so that it is adjacent to and covers at least a central portion of said first major surface of said fluff layer, wherein said fluff layer and said absorbent laminate layer are connected to each other by a plurality of channel regions consisting of compressed, physically integrated portions of said fluff layer and of said absorbent laminate layer, the channel regions having a given density and, between the channel regions, discrete regions composed of portions of said fluff layer and of said absorbent laminate layer having a density less than the given density, said channel regions having been formed by pressing absorbent laminate into a moistened surface of the fluff layer, and the absorbent core has improved absorbency as a consequence of said channel regions, and is operable to absorb, through said cover sheet, multiple wettings with simulated urine in quantities which would cause gel blocking in the absence of said channel regions, and a water impervious backing sheet positioned adjacent the second surface of said absorbent fluff layer.

15. The absorbent product of claim 14 wherein said absorbent core further comprises a tissue sheet which is positioned between said fluff layer and said backing sheet.

16. An absorbent core including a super absorbent polymer, said core consisting essentially of a water permeable cover sheet, an absorbent fluff layer having first and second major surfaces, the first surface being positioned adjacent to said cover sheet, a layer of tissue disposed between the first major surface of said fluff layer and said cover sheet, and super absorbent polymer powder distributed in said fluff layer, adjacent to the first major surface, wherein said fluff and tissue layers are connected to each other by a plurality of channel regions consisting of compressed, physically integrated portions of the fluff and tissue layers having a given density and, between the channel regions, discrete regions of portions of said fluff and tissue layers having a density less than the given density, said channel regions having been formed by pressing the tissue layer into a surface of the fluff layer to which an adhesive has been applied, and the absorbent core has improved absorbency as a consequence of said channel regions, and is operable to absorb, through said cover sheet, multiple wettings with simulated urine in quantities which would cause gel blocking in the absence of said channel regions.

17. The absorbent core claimed in claim 16 in which the second major surface of said fluff layer is substantially smooth, while the channel regions in the physically integrated portions of said fluff layer and said absorbent laminate layer are diamond shaped.

18. The absorbent core claimed in claim 16 wherein the channel regions are arranged in a repeating diamond shaped pattern.

19. An absorbent product consisting essentially of an absorbent core including a super absorbent polymer, said core consisting essentially of a water permeable cover sheet, an absorbent fluff layer having first and second major surfaces, the first surface being positioned adjacent to said cover sheet, a layer of tissue disposed between the first major surface of said fluff layer and said cover sheet, and super absorbent polymer powder distributed in said fluff layer, adjacent to the first major surface, wherein said fluff and tissue layers are connected to each other by a plurality of channel regions consisting of compressed, physically integrated portions of the fluff and tissue layers having a given density and, between the channel regions, discrete regions of portions of said fluff and tissue layers having a density less than the given density, said channel regions having been formed by pressing the tissue layer into a surface of the fluff layer to which an adhesive has been applied, and the absorbent core has improved absorbency as a consequence of said channel regions, and is operable to absorb, through said cover sheet, multiple wettings with simulated urine in quantities which would cause gel blocking in the absence of said channel regions, and a water impervious backing sheet positioned adjacent the second surface of said absorbent fluff layer.

20. The absorbent product of claim 19 wherein said absorbent core further comprises first and second tissue sheets, said first tissue sheet being positioned between said fluff layer and said backing sheet, said second tissue sheet being positioned between said absorbent laminate layer and said cover sheet, and said second tissue sheet being integrated by the pressing operation into the higher density channel regions of the absorbent core.

* * * * *